(12) United States Patent
Pinchuk et al.

(10) Patent No.: US 11,666,360 B2
(45) Date of Patent: Jun. 6, 2023

(54) TOOL(S) FOR INSERTING A GLAUCOMA SHUNT

(71) Applicant: INNFOCUS, INC., Miami, FL (US)

(72) Inventors: Leonard Pinchuk, Miami, FL (US); John B. Martin, Miami, FL (US); Anh Le, Miami Lakes, FL (US)

(73) Assignee: INNFOCUS, INC., Miami, FL (US)

( * ) Notice: Subject to any disclaimer, the term of this patent is extended or adjusted under 35 U.S.C. 154(b) by 960 days.

(21) Appl. No.: 16/327,450

(22) PCT Filed: Aug. 24, 2017

(86) PCT No.: PCT/US2017/048431
§ 371 (c)(1),
(2) Date: Feb. 22, 2019

(87) PCT Pub. No.: WO2018/044684
PCT Pub. Date: Mar. 8, 2018

(65) Prior Publication Data
US 2021/0045772 A1 Feb. 18, 2021

Related U.S. Application Data

(60) Provisional application No. 62/382,641, filed on Sep. 1, 2016.

(51) Int. Cl.
*A61B 17/34* (2006.01)
*A61F 9/007* (2006.01)
*A61B 17/32* (2006.01)

(52) U.S. Cl.
CPC ...... *A61B 17/3468* (2013.01); *A61F 9/00781* (2013.01); *A61B 2017/320056* (2013.01)

(58) Field of Classification Search
CPC ..... A61B 17/3468; A61B 2017/320056; A61F 9/00781; A61F 9/0017; A61F 9/007; A61F 9/0008; A61M 2210/0612; A61M 27/002
See application file for complete search history.

(56) References Cited

U.S. PATENT DOCUMENTS 5,092,837 A * 3/1992 Ritch ................ A61F 9/00781
604/294
5,180,362 A * 1/1993 Worst ................ A61F 9/00781
604/294

(Continued)

OTHER PUBLICATIONS

International Search Report and Written Opinion of Application No. PCT/US/ 17/48431 dated Dec. 29, 2017.

*Primary Examiner* — Adam Marcetich
*Assistant Examiner* — Rachel O'Connell
(74) *Attorney, Agent, or Firm* — Gordon & Jacobson, P.C.

(57) ABSTRACT

A glaucoma treatment system includes a glaucoma drainage device having a flexible tube with distal and proximal ends, and an inserter with a filament that extends beyond the distal end of a rigid elongate member (e.g., rod or inserter tube). The filament is configured to detachably couple a distal portion of the drainage device tube to the elongate member of the inserter. The filament may extend through a wall of the distal portion of the drainage device tube. The filament and elongate member of the inserter can be configured for relative movement to detach the drainage device tube from the inserter. The elongate member can define an internal channel, and the filament can be configured for axial movement in this channel so that the filament may move toward the proximal end of the elongate member to detach the drainage device tube from the inserter. Other tools are described and claimed.

31 Claims, 18 Drawing Sheets

(56) References Cited

U.S. PATENT DOCUMENTS

| | | | |
|---|---|---|---|
| 5,683,408 A | 11/1997 | De Laage De Meux et al. | |
| 5,741,292 A | 4/1998 | Mendius | |
| 7,431,709 B2 | 10/2008 | Pinchuk et al. | |
| 7,594,899 B2 | 9/2009 | Pinchuk et al. | |
| 7,837,644 B2 | 11/2010 | Pinchuk et al. | |
| 9,044,301 B1 | 6/2015 | Pinchuk et al. | |
| 9,101,444 B2 | 8/2015 | Pinchuk | |
| 2002/0133168 A1 | 9/2002 | Smedley et al. | |
| 2004/0068286 A1 | 4/2004 | Mendius | |
| 2013/0184631 A1* | 7/2013 | Pinchuk | A61F 9/00781 604/8 |
| 2014/0371651 A1* | 12/2014 | Pinchuk | A61F 9/00781 606/108 |
| 2015/0133946 A1* | 5/2015 | Horvath | A61M 27/002 606/108 |
| 2015/0148729 A1* | 5/2015 | Pinchuk | A61M 27/002 604/8 |

* cited by examiner

PRIOR ART   PRIOR ART

TOOL(S) FOR INSERTING A GLAUCOMA SHUNT

BACKGROUND

1. Field

The present disclosure relates to the treatment of glaucoma, and more particularly, to medical devices and methods for creating a drainage pathway to divert aqueous humor out of the anterior chamber of the eye such that pressure within the eye is reduced.

2. State of the Art

FIGS. 1A and 1B show a glaucoma shunt described in detail in U.S. Pat. Nos. 9,101,444; 9,044,301; 7,837,644; 7,594,899; and 7,431,709, herein incorporated by reference in their entireties. The glaucoma shunt 1 consists of an elongated tube 2 with two opposed protrusions or fins 3A, 3B (collectively, fins 3). The fins 3 extend radially in two opposed directions transverse to the axis of the tube 2. FIG. 1B shows fin 3B, which extends in the direction out of the page and transverse to the axis of the tube 2. Fin 3A is not show in this figure, but it extends in the direction into the page and transverse to the axis of the tube 2. The fins 3 also extend beyond the outer surface of the tube 2 as best shown in FIG. 1A. The tube 2 defines a lumen 4 that extends down the entire length of the tube 2 between its distal end 5 and opposed proximal end 6. The distal end 5 can be cut in a bevel shape as shown.

FIG. 2 shows a human eye 20 with a needle 21 inserted under the limbus 22 into the anterior chamber 23. The needle 21 can have an outer diameter in the range from 30-G to 20-G (preferably 25-G). The needle 21 is used to create a needle or tissue tract 24 under the limbus 22 that leads to the anterior chamber 23 when the needle 21 is removed from the eye 20. The needle 21 can be inserted through the conjunctiva and sclera under the limbus 22 and into the anterior chamber 23. Alternatively, the sclera can be exposed by forming a flap under the conjunctiva and under the Tenons membrane (also called Tenon's Capsule), and the needle 21 can be inserted through the sclera, under the limbus 22 and into the anterior chamber 23.

Once the needle or tissue tract 24 is formed, the glaucoma shunt 1 is placed into the needle tract 24 as shown in FIG. 3. In this implanted configuration, the distal end 5 of the tube, shown without the bevel, 2 lies in the anterior chamber 23, and the lumen 4 of the tube 2 drains aqueous humor from the anterior chamber 23 to a drainage location adjacent the proximal end 6 of the tube 2. Flow from the anterior chamber 23 to this drainage location lowers intraocular pressure in the eye. In this implanted configuration, the proximal end 6 of the tube 2 is located distally relative to the anterior chamber 23 of the eye. The fins 3 can form a sealing interface to the ocular tissue of the needle tract 24 in order to limit peri-annular leakage of aqueous humor that can possibly flow between the exterior surface of the tube 2 and the ocular tissue of the needle tract 24. The fins 3 can also aid in fixating the glaucoma shunt 1 in the implanted configuration by resisting movement of the glaucoma shunt 1 through the needle tract 24 toward the anterior chamber 23 of the eye.

The introduction of the glaucoma shunt 1 into the needle tract 24 can be accomplished with the use of a forceps (not shown). Although this insertion maneuver functions most of the time, it is a relatively difficult and slow procedure to perform as the glaucoma shunt 1 is very soft with minimal longitudinal stiffness, which can cause the shunt 1 to buckle at the shunt 1 is maneuvered through the needle tract 24, which can be especially difficult if stray collagen fibers cross the needle tract 24. It can best be described as like "pushing a rope." The glaucoma shunt 1 needs to be grasped with the forceps close to the distal end and gently nudged down the needle tract 24. It was found in clinical studies that this procedure functions about 80% of the time: the remaining 20% of the time requires reinserting the needle 21 to smooth the needle tract 24 to better effectuate insertion of the glaucoma shunt 1.

SUMMARY

Systems and methods are described that enable implanting an elongate glaucoma drainage device in a relatively simple and reproducible manner. The procedures can be performed in combination with cataract surgery or on its own.

In embodiment(s), the instruments used in the methods include a syringe, a tissue tract forming device (e.g., a needle or knife) and an inserter, all for implanting the glaucoma drainage device. Some or all of the instruments may be provided as a kit, with or without the glaucoma drainage device. The inserter can be provided in a kit with the glaucoma drainage device, as they are used together to implant the glaucoma drainage device. The glaucoma drainage device includes an elongate tube that defines an internal lumen extending along the length of the tube between its distal end and proximal end. The glaucoma drainage device can also include one or more protrusions or fins spaced from the distal and proximal ends of the tube and extending radially outward beyond the exterior surface of the tube. The protrusion(s) or fins) can provide a sealing interface to ocular tissue to limit leakage of aqueous humor between the tube and the ocular tissue. The protrusion(s) or fin(s) can also aid in fixating the glaucoma drainage device in its desired implanted configuration in the eye. The inserter includes an elongate member (such as rod or tube) with a filament that extends beyond the distal end of the elongate member. The filament is detachably coupled to a distal portion of the tube of the glaucoma drainage device. The filament can extend through a wall of the distal portion of the tube of the glaucoma drainage device.

The elongate member of the inserter is rigid, while the tube of the glaucoma drainage device is flexible. As used herein, "rigid" means that the elongate member of the inserter will not bend or buckle under a range of forces (e.g., axial compressive forces) that may be imparted to the elongate member of the inserter by the hand of the user when the elongate member is inserted into a tissue tract leading to the anterior chamber of the eye, as described in greater detail below. Also, as used herein, "flexible" means that the tube of the glaucoma drainage device, if unsupported, will bend or buckle under the axial compressive threes that may be imparted on the tube of the glaucoma drainage device by the hand of the user when the tube of the glaucoma device alone is pushed into a tissue tract leading to the anterior chamber of the eye.

In embodiment(s), the distal portion of the filament of the inserter can be bent toward the proximal end of the elongate member of the inserter. Alternatively, the distal portion of the filament of the inserter can be bent in a loop that detachably couples the tube of the glaucoma drainage device to the elongate member of the inserter.

In embodiment(s), the filament can be configured to move relative to the elongate member of the inserter proximally toward the proximal end of the elongate member in order to release or detach the tube of the glaucoma drainage device from the filament and the elongate member of the inserter. For example, elongate member of the inserter can be an inserter tube that defines an internal channel, and the filament can move axially in the channel of the inserter tube toward the proximal end of the inserter tube in order to release (decouple) or detach the tube of the glaucoma drainage device from the filament and the elongate member of the inserter.

In one embodiment, a hub can be positioned adjacent the proximal end of the inserter tube, and a proximal end of the filament can be secured to the hub. A retainer can be secured to the outer surface of the inserter tube at an intermediate position between the distal end of the inserter tube and the hub. Also, a spring may surround the outer surface of the inserter tube between the hub and the retainer. The hub and spring can be configured for displacement relative to the inserter tube where the spring is biased in compression to produce tension in the filament to cause the filament to secure the tube of the glaucoma drainage device to the distal end of the inserter tube in a first configuration of the hub and the spring. The hub and spring are reconfigurable from the first configuration to a second configuration by moving the hub and spring towards the retainer, thereby causing the filament to move axially in the channel of the inserter tube toward the proximal end of the inserter tube in order to release (decouple) or detach the tube of the glaucoma drainage device from the filament and the elongate member of the inserter.

In another embodiment, a scissor mechanism can be coupled between a proximal end of the inserter tube and to a proximal end of the filament. The scissor mechanism has handles operable to move the filament axially in the channel of the inserter tube toward the proximal end of the inserter tube in order to release (decouple) or detach the tube of the glaucoma drainage device from the filament and the elongate member of the inserter.

In yet another embodiment, a filament-form actuator can be connected between a proximal end of the inserter tube and a proximal end of the filament. The filament-form actuator is configured to be pinched or otherwise compressed to move the filament axially in the channel of the inserter tube toward the proximal end of the inserter tube in order to release (decouple) or detach the tube of the glaucoma drainage device from the filament and the elongate member of the inserter.

In embodiment(s), a proximal portion of the tube of the glaucoma drainage device can be removably secured or tethered to the elongate member of the inserter. For example, a tether filament or sheath can be provided to removably secure the proximal portion of the tube of the glaucoma drainage device to the elongate member of the inserter. In one embodiment, the sheath can be provided with at least one bore that accommodates both the proximal portion of the tube of the glaucoma drainage device and the elongate member of the inserter. In another embodiment, the tether filament can be provided with one end of the tether filament being disposed in the lumen of the proximal end of the tube of the glaucoma drainage device and another end of the tether filament being wrapped around the elongate member of the inserter.

In embodiment(s), the elongate member of the inserter can have an outer diameter of between 0.006 inch to 0.020 inch, and may have an inner diameter of between 0.002 inch to 0.012 inch. The elongate member of the inserter is rigid as compared to the flexible nature of the tube of the glaucoma drainage device. For example, the elongate member of the inserter can be configured to withstand a concentric compressible axial load between 0.004 pound force to 0.5 pound force without experiencing inelastic deformation (e.g., buckling), while the tube of the glaucoma drainage device buckles under a concentric compressible axial load much less than 0.004 pound forces.

Prior to insertion of the glaucoma drainage device into the eye, a needle connected to a syringe may be inserted into Tenon's capsule, and a fluid injected from the syringe into Tenon's capsule to expand Tenon's capsule. In addition, the conjunctiva can be incised and a tract formed using blunt dissection under the conjunctiva and Tenon's capsule to expose the sclera. The tissue tract forming device is then inserted through the sclera, under the limbus, exiting between the cornea and the iris to form a first tissue passageway (or tissue tract) leading into the anterior chamber of the eye. With the tissue tract formed, the insertion procedure may proceed as follows.

With the filament of the inserter securing the distal portion of the tube of the glaucoma drainage device to the inserter, the distal portion of the tube of the glaucoma drainage device and the distal portion of the inserter (including the filament and distal end of the elongate member of the inserter) are introduced together into and through the tissue tract by pushing the rigid inserter into and through the tissue tract. This operation, in effect, pulls the distal portion of the glaucoma drainage device into and through the tissue tract. This operation is continued until the glaucoma drainage device is located at a desired implanted position within the tissue tract. In this implanted position, the distal end of the tube of the glaucoma drainage device can be located within the anterior chamber such that the lumen of the tube can drain aqueous humor from the anterior chamber of the eye. Furthermore, the protrusion(s) or fin(s) of the glaucoma drainage device can form a sealing interface to the ocular tissue of the needle tract in order to limit peri-annular leakage of aqueous humor that can possibly flow between the exterior surface of the tube and the ocular tissue of the needle tract. The protrusion(s) or fin(s) of the glaucoma drainage device can also aid in fixating the glaucoma drainage device by resisting movement of the glaucoma drainage device through the needle tract toward the anterior chamber of the eye.

With the glaucoma drainage device located at the desired implanted position within the tissue tract, the filament of the inserter can be released (decoupled) or detached from the distal portion of the tube of the glaucoma drainage device. In one embodiment, this can be accomplished by retracting (pulling) the elongate member of the inserter out of the tissue tract while holding the glaucoma drainage device in place. In another embodiment, the filament can be moved relative to the elongate member of the inserter proximally toward the proximal end of the elongate member in order to release (decouple) or detach the filament from the tube of the glaucoma drainage device. In either case, the entire inserter can then be removed from the tissue tract by retracting (pulling) the elongate member of the inserter out of the tissue tract while holding the glaucoma drainage device in place.

In another aspect, an ocular surgical instrument is provided for forming the tissue tract through which the inserter and glaucoma drainage device are inserted. The instrument includes a knife having a plurality of blades. The knife extends from a distal end to a proximal end along a knife axis. The knife has a first portion, a second portion, and an intermediate portion extending between the first and second portions. The first portion is located at the distal end and the second portion is spaced proximally from the first portion by the intermediate portion. The intermediate portion has a dull edge that is not configured to cut ocular tissue. The first portion has a first set of blades that extend at a first angle relative to the knife axis from a first leading blade end to a first trailing blade end at a first transverse distance from the knife axis. The second portion has a second set of blades that extend at a second angle relative to the knife axis from a second leading blade end to a second trailing blade end at a second transverse distance from the knife axis that is larger than the first transverse distance.

The first transverse distance may be between 0.015 to 0.025 inch and the second transverse distance may be between 0.03 to 0.05 inch. The first and second angles may be non-zero, acute angles. The intermediate portion may have a length along the knife axis that is 2.0 mm (0.08") to 2.4 mm (0.1").

DETAILED DESCRIPTION OF THE PREFERRED EMBODIMENTS

The embodiments of the present disclosure provide an apparatus and corresponding method for effective insertion of the glaucoma shunt 1 into the needle tract 24 where the glaucoma shunt 1 is used to drain aqueous humor from the anterior chamber 23 of the eye to reduce elevated intraocular pressure of the eye.

Figures 1A, 1B:
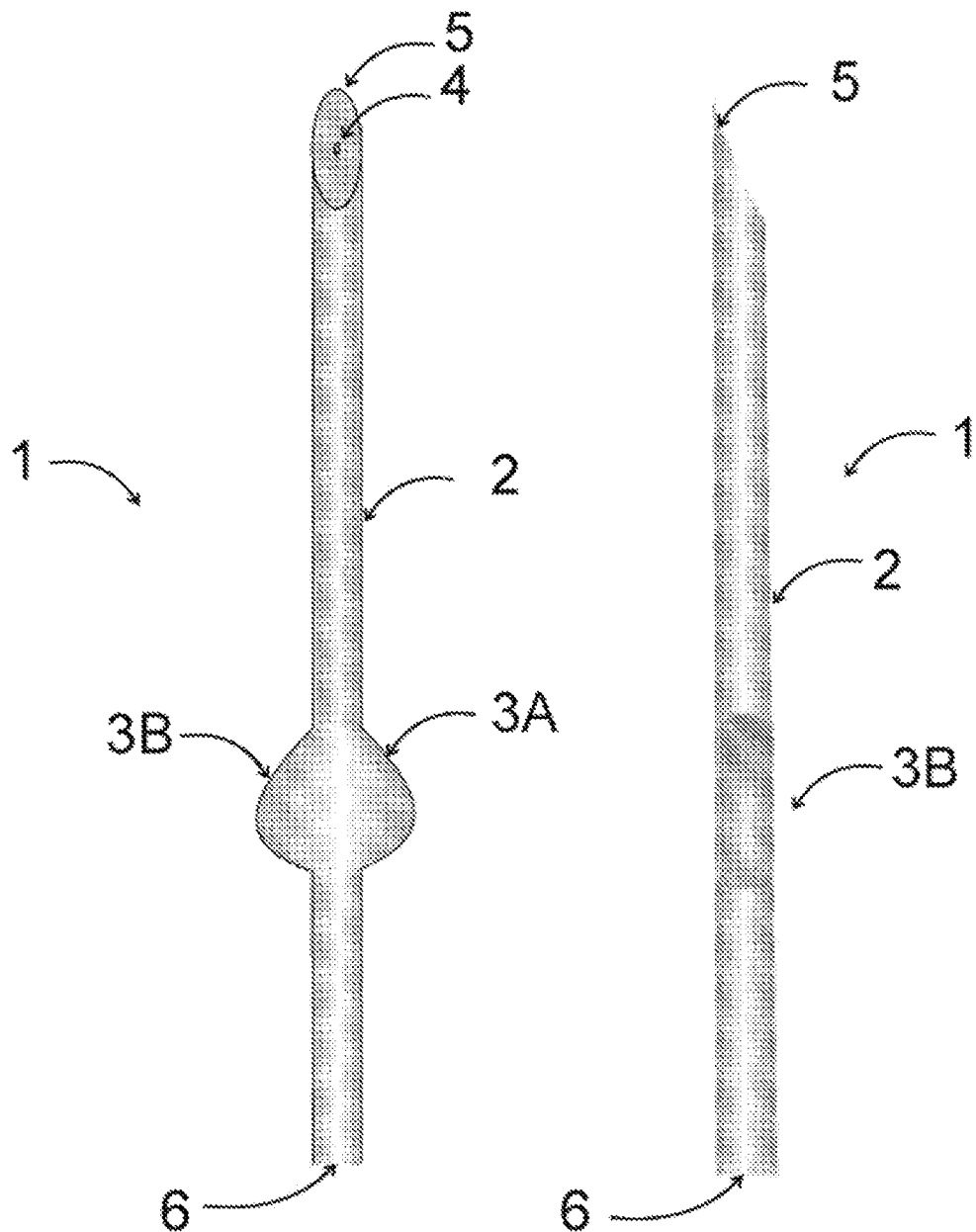
FIGS. 1A and 1B are plan and side views of a glaucoma shunt described in detail in U.S. Pat. Nos. 9,101,444; 9,044,301; 7,837,644; 7,594,899; and 7,431,709.
Figure 2:
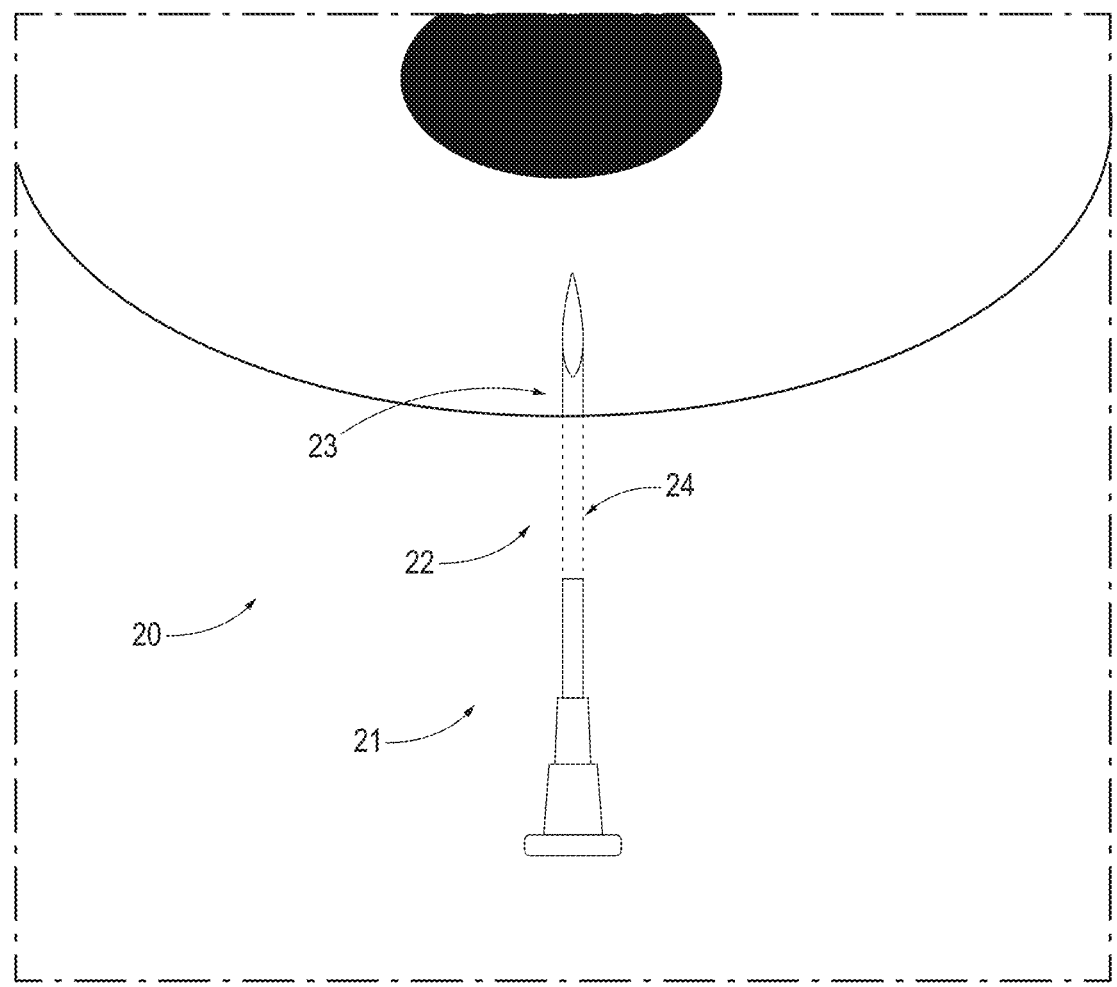
FIG. 2 shows a human eye with a needle inserted under the limbus into the anterior chamber.
Figure 3:
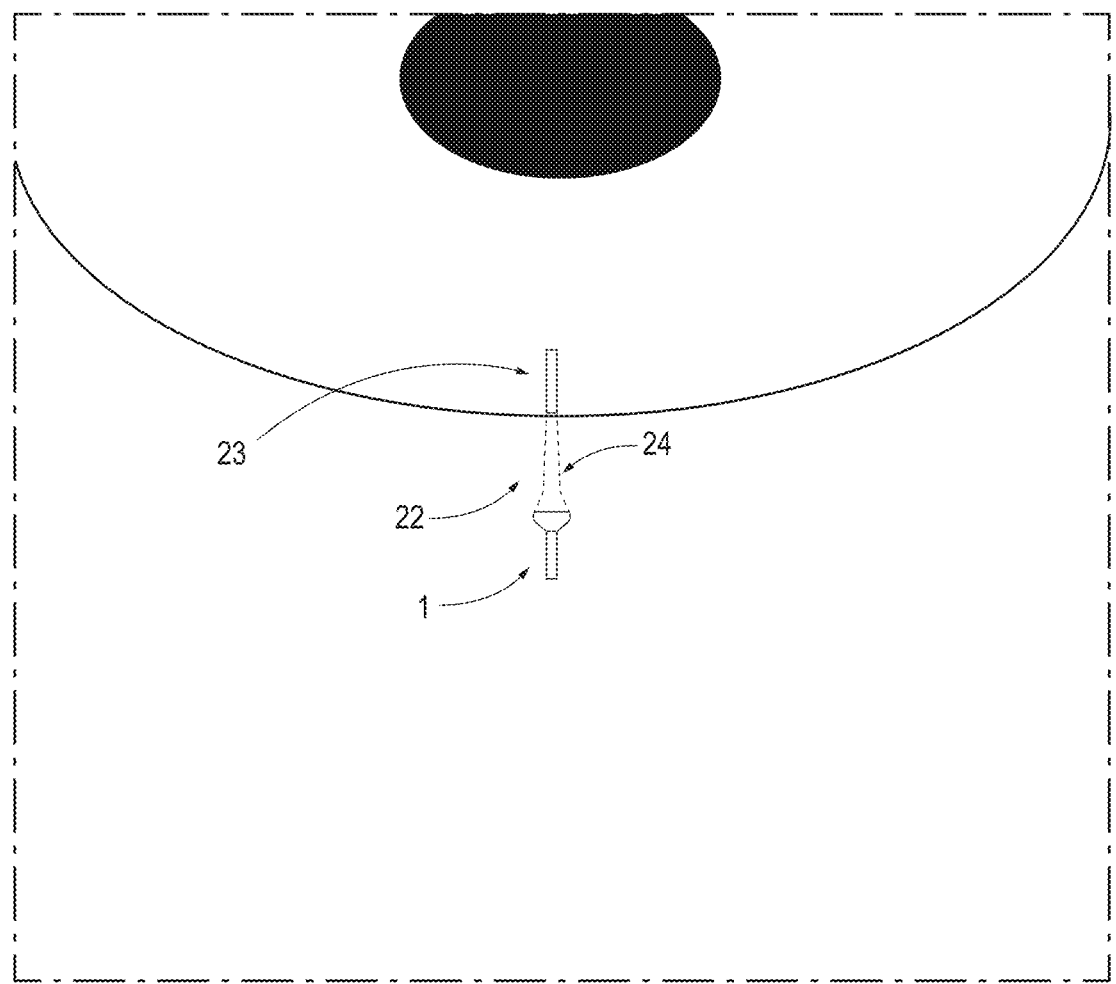
FIG. 3 shows the glaucoma shunt placed into the needle tract formed by the needle of FIG. 2.
Figure 4A:
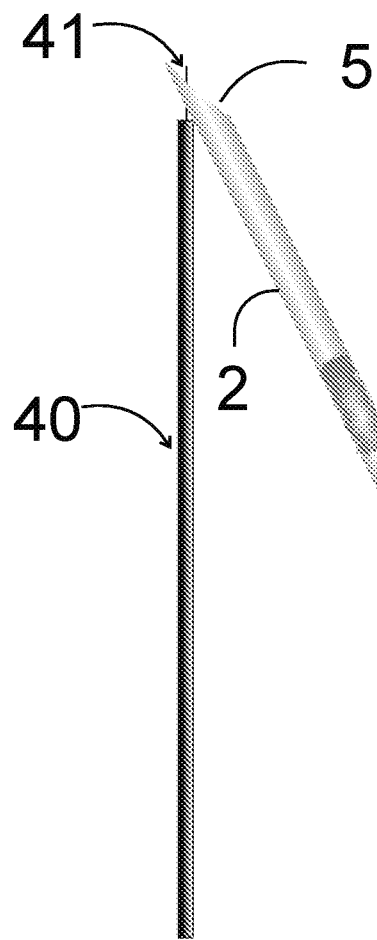
FIGS. 4A, 4B, and 4C illustrate an embodiment of an inserter apparatus in accordance with this disclosure for insertion of the glaucoma shunt into the needle tract of FIG. 3.
Figure 4B:
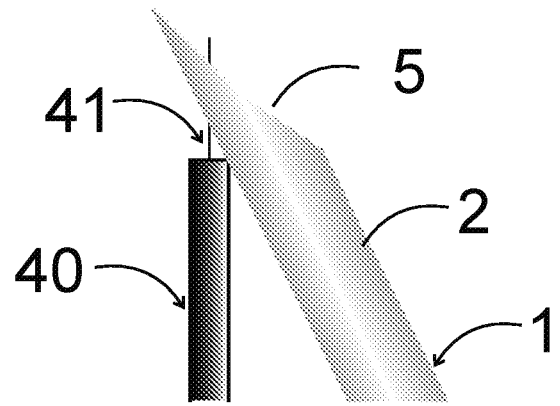
Figure 4C:
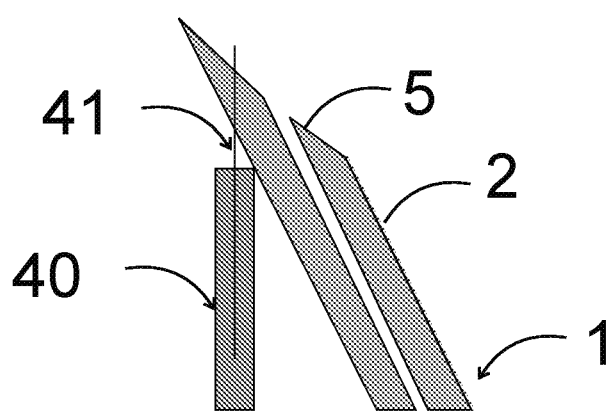

FIGS. 4A, 4B, and 4C illustrate an embodiment of an inserter apparatus for insertion of the glaucoma shunt 1 into the needle tract 24. The inserter apparatus includes a thin filament 41 that is attached or secured at or near the distal end of an elongate rod 40 such that the filament 41 extends from the distal end of the rod 40. The filament 41 may be a thin filament or thread. The filament 41 may be solid or hollow and may be a single filament (monofilament) or be formed as a bundle of filaments 41 arranged in parallel or in a braid. The rod 40 can be a solid rod or preferably a hollow rod or tube. The outer diameter of the rod 40 is much larger than the thickness of the filament 41, and the length of the rod 40 is much larger than the length of the filament 41 that extends from the distal end of the rod 40. The length of the filament 41 that extends from the distal end of the rod 40 is pushed through the distal end 5 of the tube 2 of the shunt 1 such that the filament 41 penetrates partially or completely through the wall of the distal end 5 of the tube 2 as best shown in FIGS. 4B and 4C. This causes the distal end 5 of the tube 2 to be detachably coupled or attached to the distal end of the rod 40. The longitudinal stiffness (or columnar strength) of the rod 40 is much greater than longitudinal stiffness of the soft flexible shunt 1. The distal end of the rod 40 acts as a shoulder that interfaces to the tube 2. FIG. 4B is a magnified view of the distal end of the rod 40 and the distal end of the tube 2. FIG. 4C is a magnified cross-sectional view of the distal end of the rod 40 and the distal end of the tube 2. Although FIGS. 4A, 4B and 4C show the distal end or shoulder of rod 40 touching tube 1 at a single point, the distal end of rod 40 can be beveled to touch the tube in a linear manner along the bevel.

The rod 40 is rigid, while the tube 2 is flexible. As used herein, "rigid" means that the rod 40 will not bend or buckle under a range of forces (e.g., axial compressive forces that may be imparted to the rod 40 by the hand of the user when the rod 40 is inserted into a tissue tract leading to the anterior chamber of the eye, as described in greater detail below. Also, as used herein, "flexible" means that the tube 2, if unsupported, will bend or buckle under the axial compressive forces that may be imparted on the tube 2 by the hand of the user when the tube 2 is pushed into a tissue tract leading to the anterior chamber of the eye.

In one embodiment, the rod 40 can be formed from medical grade stainless steel hypodermic tubing. Exemplary suitable tubing sizes range from 34 RW (regular wall gauge), which has a 0.006 inch outer diameter and 0.002 inch inner diameter, to 25TW (thin wall gauge), which has a 0.020 inch outer diameter and a 0.012 inch inner diameter. One particular tubing size range is from 33RW (regular wall gauge) which has an 0.008 inch outer diameter and 0.004 inch inner diameter, to 31 RW (regular wall gauge), which has 0.010 inch outer diameter and a 0.005 inch inner diameter. Another particular tubing size range has outer diameter 0.008 to 0.012 inch (preferably 0.009 inch) with an inner diameter 0.003 to 0.006 inch (preferably 0.004 inches). Note that these aforementioned tube sizes are commercially available. One skilled in the art would know that tubing of this nature can be custom extruded with optimized dimensions which may preferably be 0.003 inch inner diameter and 0.006 inch outer diameter.

Suitable hypodermic tubing used for the rod 40 can have sufficient longitudinal stiffness (or columnar strength) to introduce the glaucoma shunt 1 into the needle tract 24 as described herein without buckling or bending of the rod 40. The critical load is the maximum load which a column can bear while staying straight without buckling and is given by the formula:

$$P_{cr} = \frac{\pi^2 EI}{(KL)^2}, \quad (1)$$

where
 $P_{cr}$=Euler's critical load as a longitudinal compressive load on the column,
 E=modulus of elasticity of column material,
 I=minimum area moment of inertia of the cross section of the column,
 L=unsupported length of the column,
 K=column effective length factor based on the manner in which the ends of the column are constrained when axially compressed.

Figure 4D:
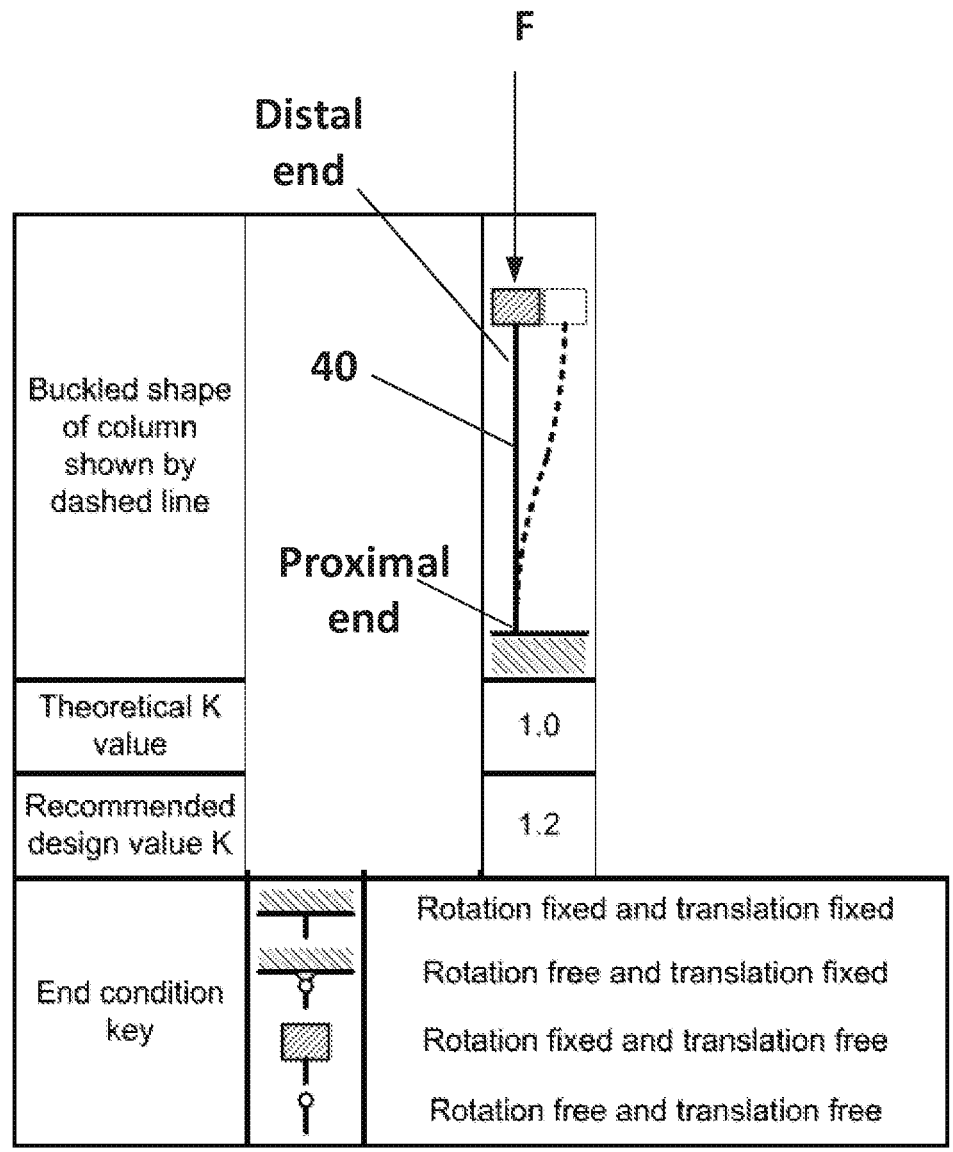
FIG. 4D shows schematic example of a compressive load test arrangement showing an axial compressive load (i.e., force "F") being applied to a portion of the inserter apparatus shown in FIGS. 4A to 4C.

Equation (1) assumes that the material of the rod 40 is homogeneous and isotropic, that the compressive load on the column is only coaxial, and that the cross-section of the column is uniform throughout its length. The moment of inertia I is a function of the cross-sectional geometry of the rod 40 and the modulus of elasticity E is based on the material properties of the rod 40. Also, in the example of rod 40, it may be assumed that the proximal end of the rod 40 is rotation-fixed and translation-fixed, meaning that the proximal end of the rod 40 is not configured to pivot or translate at that end. Also, in the example of the rod 40, it may be assumed that the distal end of the rod 40 is rotation-fixed and is translation-free, meaning that the distal end of the rod 40 is not configured to pivot at the distal end, but is free to translate relative to the central axis of the rod. Given these assumptions about the end loading constraints, the theoretical value of K in equation (1) is 1.0. A schematic example of a compressive load test arrangement showing an axial compressive load (i.e., force "F") being applied to rod 40 using these assumptions is shown in FIG. 4D.

For example, a 1.00 inch length of the hypodermic tubing suitable for rod 40 should be sufficiently stiff to prevent bending and buckling of the tubing beyond its elastic limit when inserted into the needle tract and experiencing loads. One suitable range of critical load ($P_{cr}$) for a 1 inch length of hypodermic tubing used for rod 40 is between 0.004 pound force (lbf) to 0.5 lbf, and preferably 0.013 lbf to 0.033 lbf. Preferably, the hypodermic tubing suitable for rod 40 has a critical load that exceeds the axial compressive loads that will be experienced by the rod 40 during use. With these mechanical properties, the rod 40 of the inserter is rigid as compared to the flexible nature of the tube of the glaucoma drainage device. Specifically, the rod 40 of the inserter is configured to withstand a concentric compressible axial load between 0.004 pound force (lbf) to 0.5 pound force (lbf) without experiencing inelastic deformation (e.g., buckling), while the tube of the glaucoma drainage device buckles under a concentric compressible axial load much less than 0.004 pound forces.

The filament 41 may be made from medical grade metals, such as stainless steel and titanium. The filament 41 may have a diameter of 0.001 to 0.003 inch and may preferably be about 0.002 inch.

Figure 5:
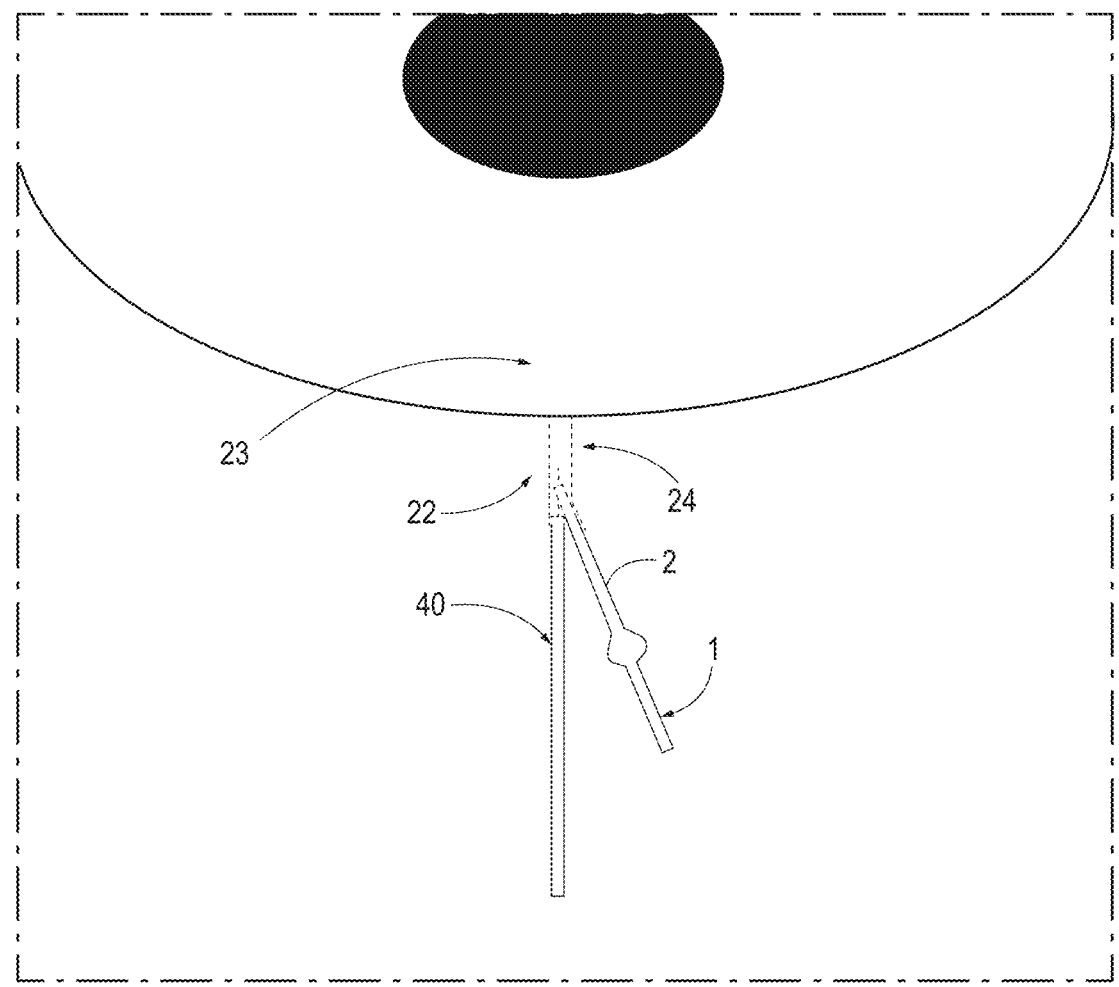
FIGS. 5, 6, and 7 show a progression of pushing the glaucoma shunt with the inserter through the needle tract of FIG. 3 to insert the distal portion of the tube of the glaucoma shunt into the needle tract.
Figure 6:
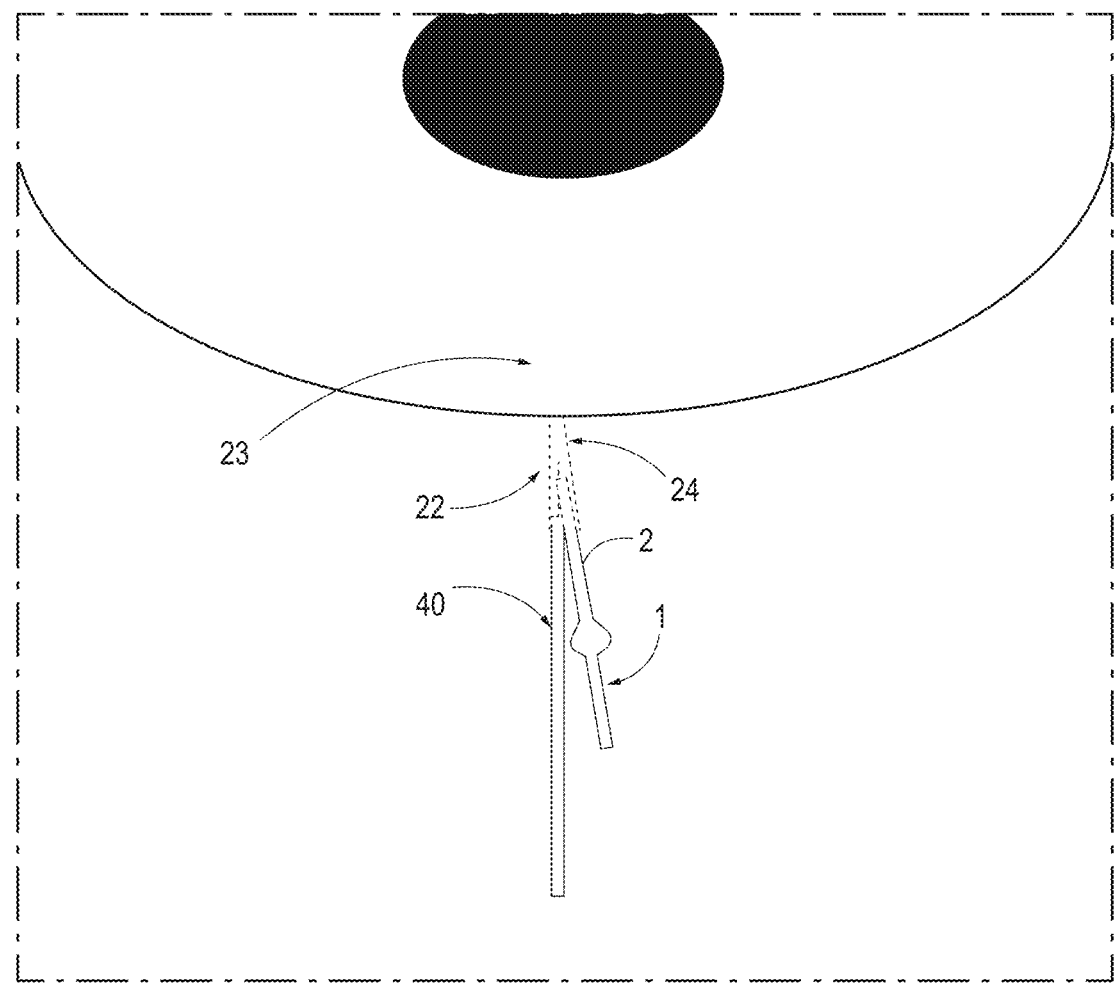
Figure 7:
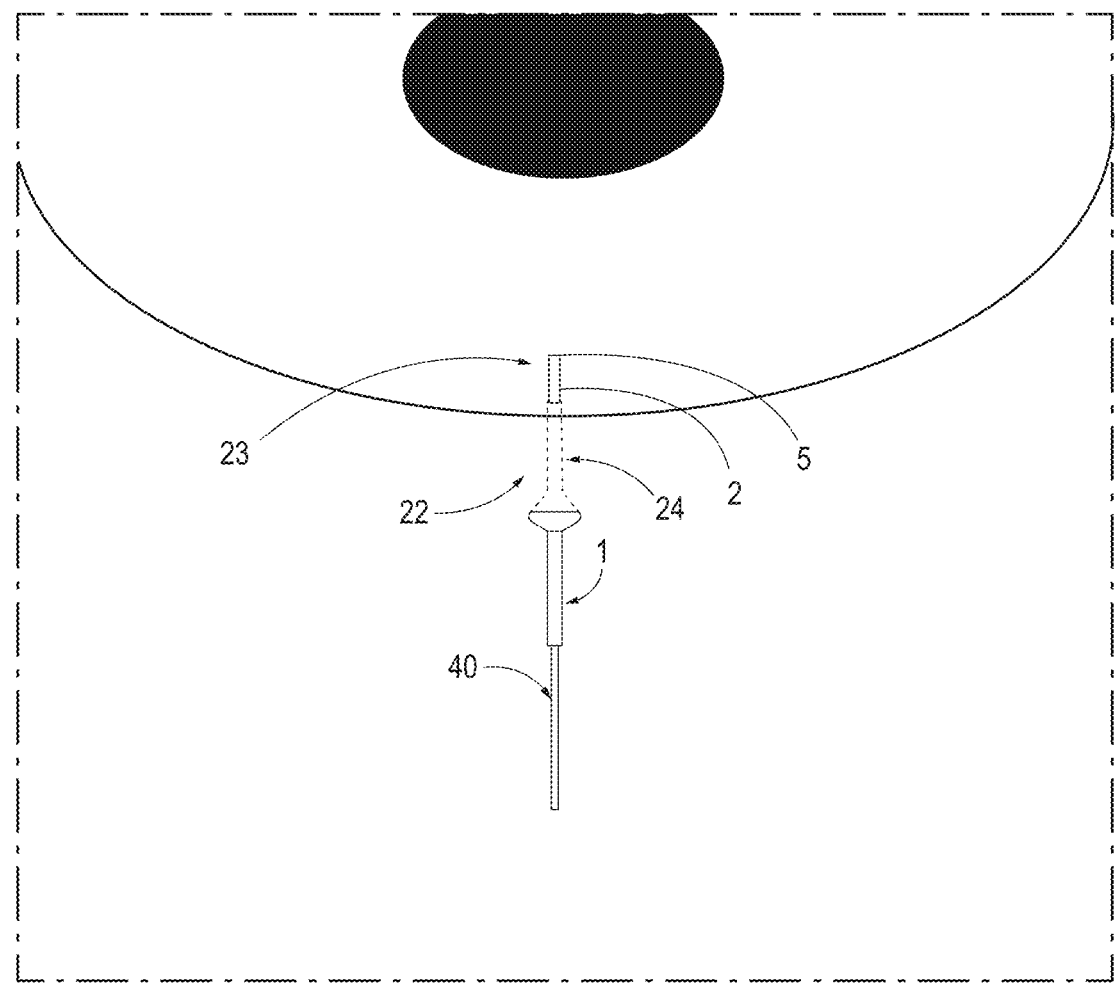

As shown in FIGS. 5, 6, and 7, with the filament 41 pushed through the distal end 5 of the tube 2, the user pushes the rod 40 through the needle tract 24 to insert both the distal portion of the glaucoma shunt 1 and the distal end of the rod 40 into the needle tract 24. In this step, the longitudinal stiffness of the rod 40 allows the rod 40 to be pushed through the needle tract 24 without buckling while the distal portion of the tube 2 (which is the distal part of the tube 2 that is proximal to the wall of distal end 5 pierced by the needle 41) is pulled through the needle tract 24. The distal end of the rod 40 acts as a shoulder that interfaces to the distal part 5 of the tube 2. Such operations avoid pushing the distal part 5 of the tube 2 through the needle tract 24, and, thus, avoid the buckling of the tube 2 that results from the pushing the glaucoma shunt 1 as described above with respect to the prior art forceps insertion methodology. Note that as the distal portion of the tube 2 is inserted into the needle tract 24, the longitudinal axis of the tube 2 aligns with longitudinal axis of the rod 40 and the distal end 5 of the tube 2 can be positioned beyond the needle tract 24 at a desired position inside the anterior chamber 23 of the eye as shown in FIG. 7.

Figure 8:
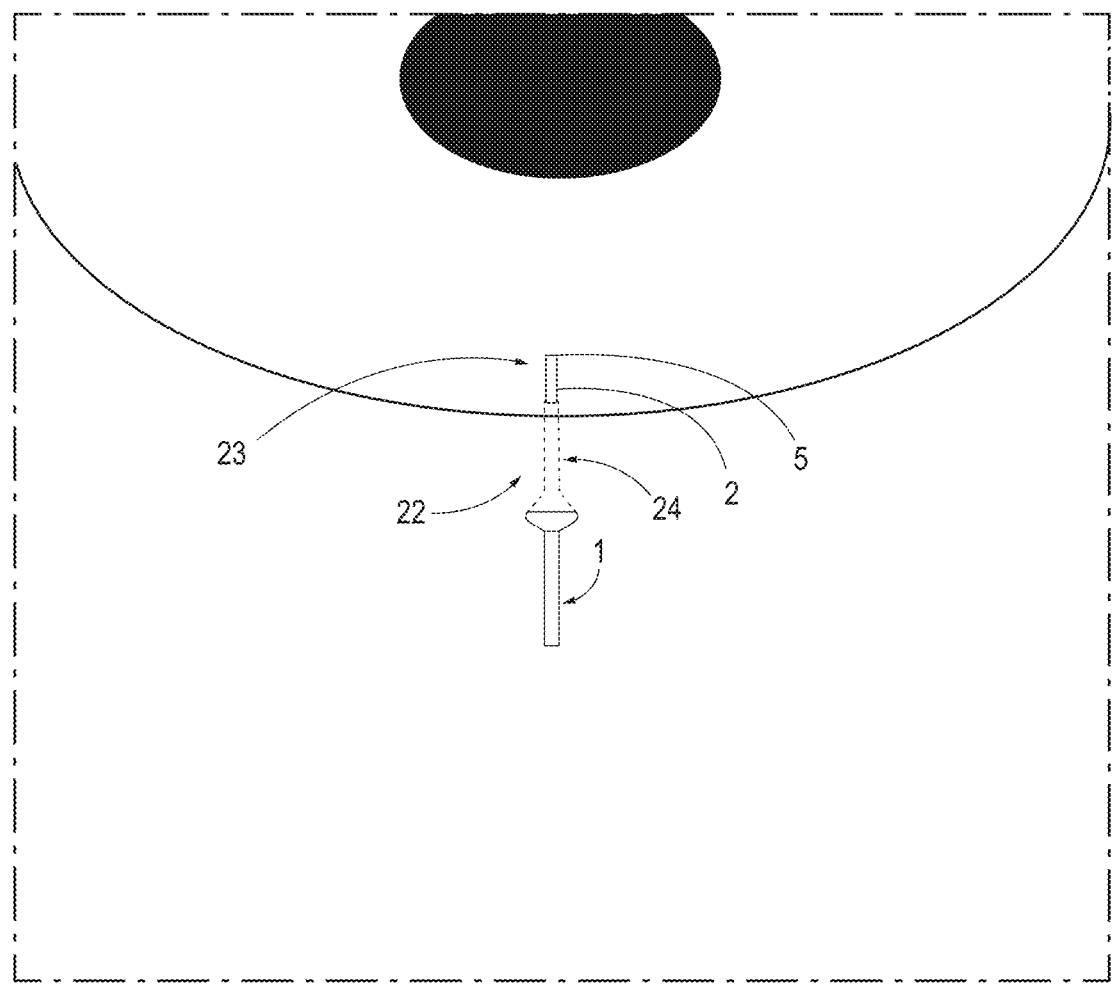
FIG. 8 illustrates a configuration where the inserter is retracted from the needle tract leaving the distal end of the tube of the glaucoma shunt positioned at a desired position inside the anterior chamber of the eye.

With the distal end 5 of the tube 2 positioned at a desired position inside the anterior chamber 23 of the eye, the user, if need be, holds the glaucoma shunt 1 secure in place and retracts the rod 40 such that the rod 40 is pulled out of the anterior chamber 23 and completely through the needle tract 24, while leaving the distal end 5 of the tube 2 in place at the desired position inside the anterior chamber 23 of the eye as shown in FIG. 8. In this implanted configuration, the lumen 4 of the tube 2 drains aqueous humor from the anterior chamber 23 of the eye to a drainage location adjacent the proximal end 6 of the tube 2 in order to avoid elevated intraocular pressure of the eye. In this implanted configuration, the proximal end 6 of the tube 2 is located distally relative to the anterior chamber 23 of the eye. In this embodiment, the distal end of the filament 41 is removed from the wall of the distal end 5 of the tube 2 in order to release or detach the tube 2 from the rod 40 and allow removal of the inserter (including the rod 40 and the filament 41) from the needle tract 24 while leaving the glaucoma shunt 1 in place.

FIGS. 9 to 14 show alternate embodiments of an apparatus for insertion of the glaucoma shunt 1 into the needle tract 24. Such inserter apparatus can be operated in a manner similar to the inserter embodiment of FIGS. 4A to 8 as described above.

Figure 9:
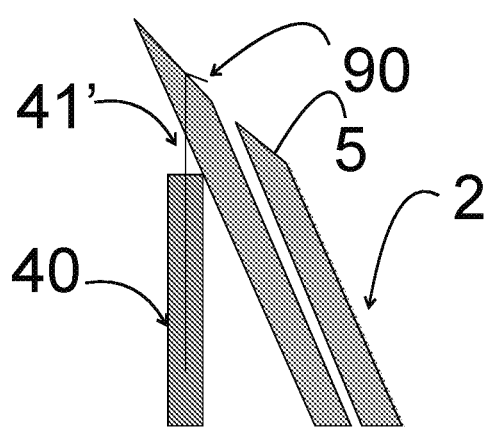
FIG. 9 shows an alternate embodiment of an inserter similar to the embodiment in FIGS. 4A to 4C where the distal portion of the filament is bent.

FIG. 9 shows an inserter similar to the embodiment of FIGS. 4A to 8 where the distal portion of the filament 41' is bent preferably toward the proximal end 6 of the tube 2. Alternatively, the distal portion of the filament 41' can be bent towards the distal end of the tube 2 or formed into a hook geometry with the end of the hook pressing into the wall of tube 2. The purpose for using a deformed filament is to help secure the tube 2 to the filament 41 during shipping and handling. In this embodiment, the bent distal portion of the filament 41' can be deformed or possibly cut or slice through the tube 2 at or near the distal end 5 of the tube 2 during retraction of the rod 40 in order to release or detach the tube 2 from the rod 40 and allow removal of the inserter (including the rod 40 and the filament 41) from the needle tract 24 while leaving the glaucoma shunt 1 in place.

Figure 10:
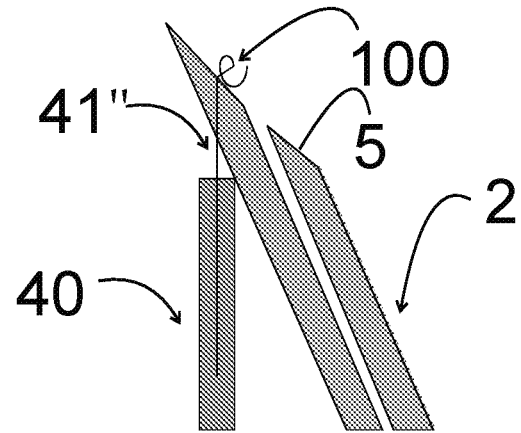
FIG. 10 shows an alternate embodiment of an inserter similar to the embodiment in FIGS. 4A to 4C where the distal portion of the filament forms a pig-tail.

FIG. 10 shows an inserter similar to the embodiment of FIGS. 4A to 9 where the distal portion of the filament 41' forms a pig-tail 100 to better secure the tube 2 to the rod 40. In this embodiment, the pigtail 100 can be deformed or possibly cut or slice through the tube 2 at or near the distal end 5 of the tube 2 during retraction of the rod 40 in order to release or detach the tube 2 from the rod 40 and allow removal of the inserter (including the rod 40 and the filament 41) from the needle tract 24 while leaving the glaucoma shunt 1 in place.

Figure 11:
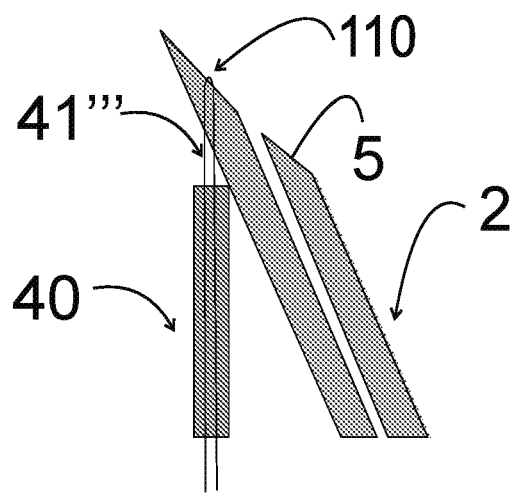
FIG. 11 shows an alternate embodiment of an inserter similar to the embodiment in FIGS. 4A to 4C where the filament is bent in a loop that secures the tube to the rod.

FIG. 11 shows an inserter similar to the embodiment of FIGS. 4A to 10 where the filament 41''' is bent in a loop 110 that secures the tube 2 to the rod 40. The loop 110 can require two holes through the wall of the tube 2 at or near the distal end 5 of the tube 2. In effect, the loop 110 stitches or fastens the tube 2 to the rod 40. In this embodiment, the loop 110 can cut or slice through the tube 2 at or near the distal end 5 of the tube 2 during retraction of the rod 40 in order to release or detach the tube 2 from the rod 40 and allow removal of the inserter (including the rod 40 and the filament 41''') from the needle tract 24 while leaving the glaucoma shunt 1 in place. Alternatively, instead of pulling the loop 110 through the tube 2 leaving a slit, one end of the filament 41''' can be cut so that an opposite end of the filament 41''' can be pulled through both holes in the tube 2 to release or detach the tube 2 from the rod 40 without cutting a slit in the tube 2. As an alternative to a filament 41 in this embodiment, the filament can be substituted with a thread or suture that can be pulled through the wall to release the tube 2. In addition, the rod 40 need not be a circular cylinder, and may instead be oval or rectangular. Further, instead of threading the loop 110 through two holes in the tube 2 as shown in FIG. 11, the loop 110 may be threaded through one hole in the wall of the tube 2 at or near the distal end 5 of the tube 2. This arrangement will cause a slit off to one side of the tube 2 when the loop 110 is pulled on with sufficient force to cut the tube 2, thereby releasing or detaching the tube 2 from the rod 40.

Figure 12:
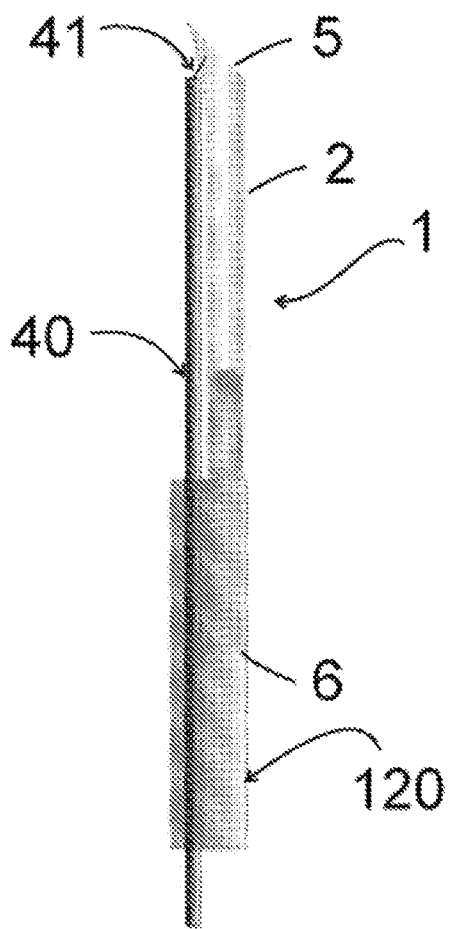
FIG. 12 shows a modification of the embodiment of FIGS. 4A, 4B, and 4C where a sheath secures or tethers a proximal part of the tube of the glaucoma shunt to the elongate member of the inserter.

FIG. 12 shows a modification of the embodiment of FIGS. 4 to 11 where the opposed end 6 of tube 2 is tethered to the rod 40 by means of a retainer sheath 120. The retainer sheath 120 can have one large bore or two bores to accommodate the proximal portion of tube 2 as well as the rod 40. The retainer sheath 120 can be a simple silicone rubber band, an extruded tube, or a machined tube. The tube 2 can also be tethered to rod 40 with sutures, threads, braids, clips, and the like. The sheath 120 can facilitate the user introducing both the distal portion of the tube 2 as well as the rod 40 into the needle tract 24. If the sheath 120 is rigidly attached to rod 40, the sheath 120 can be removed with retraction of the rod 40 from the needle tract. Tube 2 can also be removed from sheath 120 prior to retraction of the rod 40 in order to allow removal of the inserter (including the rod 40 and the filament 41) from the needle tract 24 while leaving the glaucoma shunt 1 in place.

Figure 13:
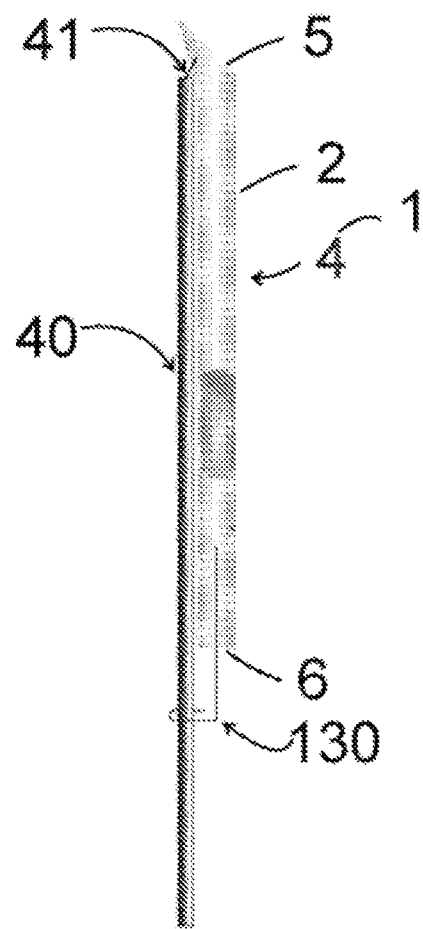
FIG. 13 shows a modification of the embodiment of FIG. 12 where a tether filament replaces the sheath in FIG. 12.

FIG. 13 shows a modification of the embodiment of FIG. 12 where a tether filament 130 replaces the sheath 120. One end of the tether filament 130 can be placed in the lumen 4 of the opposed end 6 of the tube 2, while the other end of the tether filament 130 can be wrapped around the rod 40 to secure it in place during transportation and delivery for use. The tether filament 130 can be removed from the lumen 4 of the opposed end 6 of the tube 2 prior to retraction of the rod 40 in order to allow removal of the inserter (including the rod 40 and the filament 41) from the needle tract 24 while leaving the glaucoma shunt 1 in place.

Figure 14:
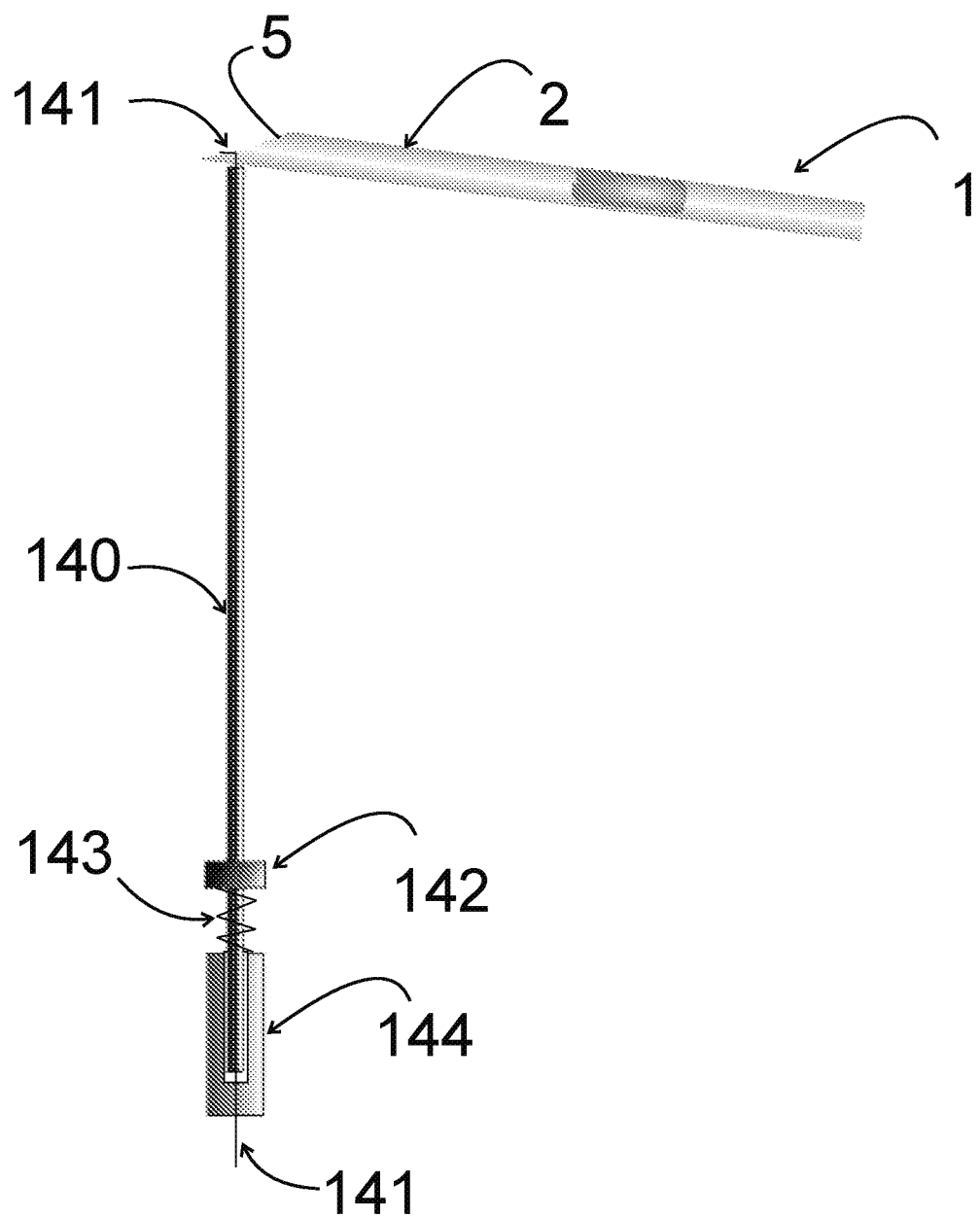
FIG. 14 shows another embodiment of an inserter tool.

FIG. 14 shows an embodiment of an inserter tool having a thin filament 141 that extends down the channel of an inserter tube 140 (hypodermic tubing). The inserter tube 140 can be formed with the same or similar dimensions and mechanical properties as described above for the inserter rod 40. The distal end of the filament 141 extends from the distal end of the inserter tube 140 and is pushed through the distal end 5 of the tube 2 of the shunt 1 such that the filament 141 penetrates partially or completely through the wall of the tube 2 at or near the distal end 5 of the tube 2 as shown. The distal end of filament 41 can be a hook, pig tail, bend, etc. In addition, the filament can be an extended loop 110 extending through Tube 2 as shown in FIG. 11. A hub 144 is positioned adjacent the proximal end of the inserter tube 140 and the proximal end of the filament 141 is secured to the hub 144. A retainer 142 is secured to the outer surface of the inserter tube 140 in an intermediate position between the distal end of the inserter tube 140 and the hub 144. The retainer 142 can be secured to the outer surface of the inserter tube 140 with an adhesive or solder/braise joint. A spring 143 surrounds the outer surface of the inserter tube 140 between the hub 144 and the retainer 142. The spring 143 is configured in compression such that it produces tension on the filament 141, which causes the filament 141 to secure the tube 2 to the distal end of the inserter tube 140. Such inserter tool can be operated in a manner similar to the embodiment of the inserter described above with respect to FIGS. 4A to 8. Once the glaucoma shunt 1 is positioned in the eye, the hub 144 is moved (i.e., by translation or sliding movement along the proximal end of the inserter tube 40) away from the retainer 142 (toward the proximal end of the inserter tube 140), which pulls the filament 141 through the wall of the tube 2 at or near the distal end 5 of the tube, thereby releasing or detaching the tube 2 from the filament 141 and the inserter tube 140. The inserter tube 140 is then removed from the needle tract 24 leaving the glaucoma shunt 1 in place. In this embodiment, the distal end of the filament 141 can be deformed or possibly cut or slice through the distal end 5 of the tube 2 during movement of the inserter tube 140 in order to release or detach the tube 2 from inserter tube 140 and allow removal of the inserter (including both the filament 141 and inserter tube 140) from the needle tract 24 while leaving the glaucoma shunt 1 in place.

Figure 15:
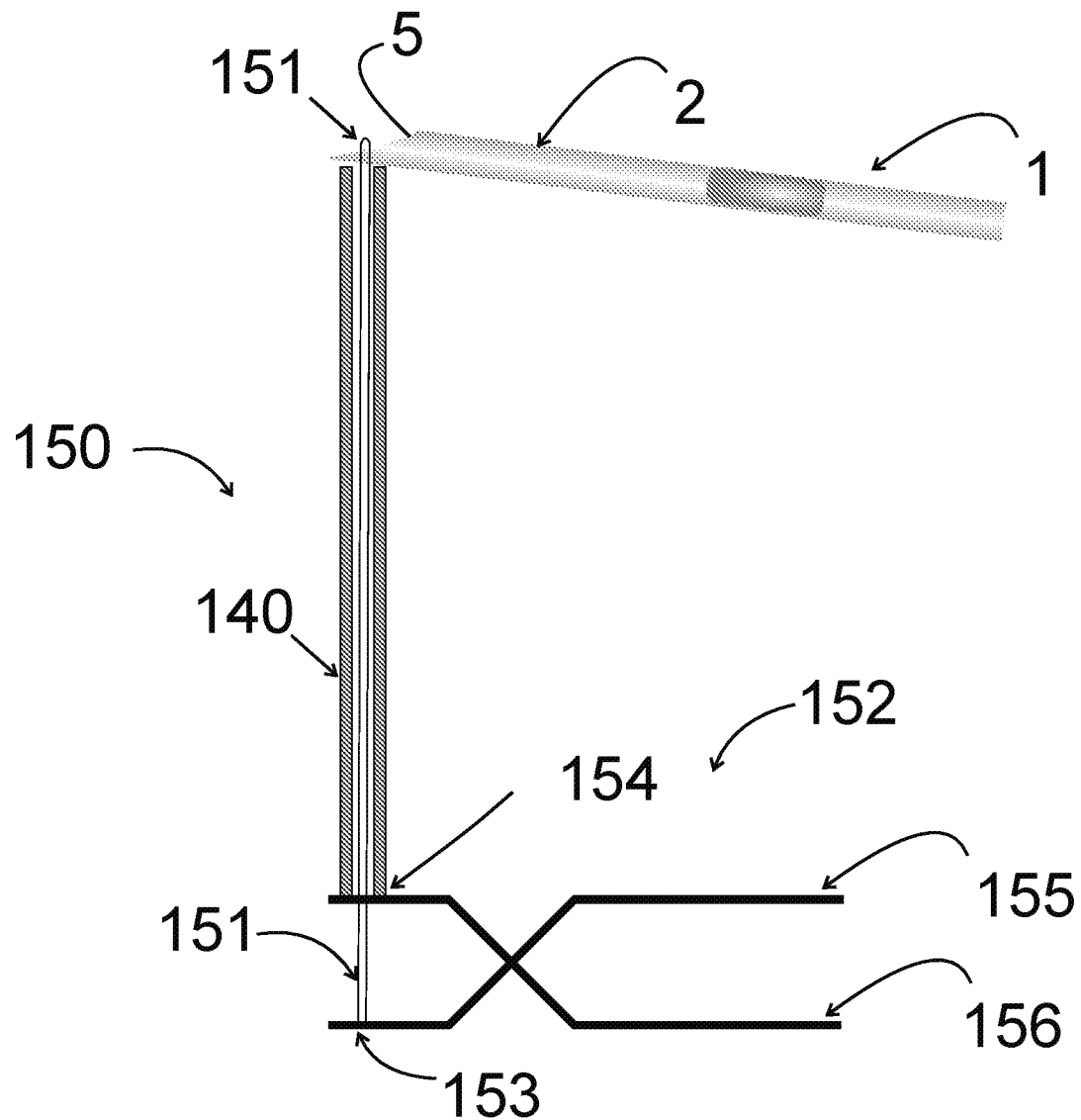
FIG. 15 shows another embodiment of an inserter tool.

FIG. 15 shows another embodiment of an inserter tool 150 having a thin filament or thread, or suture or monofilament, 151 that extends down the channel of an inserter tube 140 (hypodermic tubing). The inserter tube 140 can be formed with the same or similar dimensions and mechanical properties as described above for the inserter rod 40. In addition, the cross section of tube 140 can be circular oval or rectangular. In this embodiment, the filament 151 is looped through the wall of the tube 2 at or near the distal end 5 of the tube 2 and fed through the channel of the inserter tube 140 where it is attached or otherwise secured to a scissor mechanism 152 at 153. The filament 151 can be looped through two holes formed in the tube or one hole, similar to loop 110 in FIG. 11. The inserter tube 140 is secured to scissor mechanism 152 at 154. The scissor mechanism includes handles 155 and 156. By moving the handles 155 and 156 towards each other, the filament loop 151 is pulled (toward the proximal end of the inserter tube 140) causing the filament loop 151 to tear through the wall of the tube 2 at or near the distal end 5 of the tube 2 and release or detach the tube 2 from the filament 151 and the inserter tube 140 and allow removal of the filament 151 and inserter tube 140 from the needle tract 24 while leaving the glaucoma shunt 1 in place. Alternatively, the distal end of the filament 151 can be terminated with a bend, pig tail, hook or the like, and movement of the handles 155 and 156 towards each other can cause the distal end of the filament 151 to deform or tear through the wall of the tube 2 at or near the distal end 5 of the tube 2 in order to release or detach the tube 2 from the filament 151 and the inserter tube 141 and allow removal of the inserter 150 (including the filament 151 and inserter tube 140) from the needle tract 24 while leaving the glaucoma shunt 1 in place.

Figure 16:
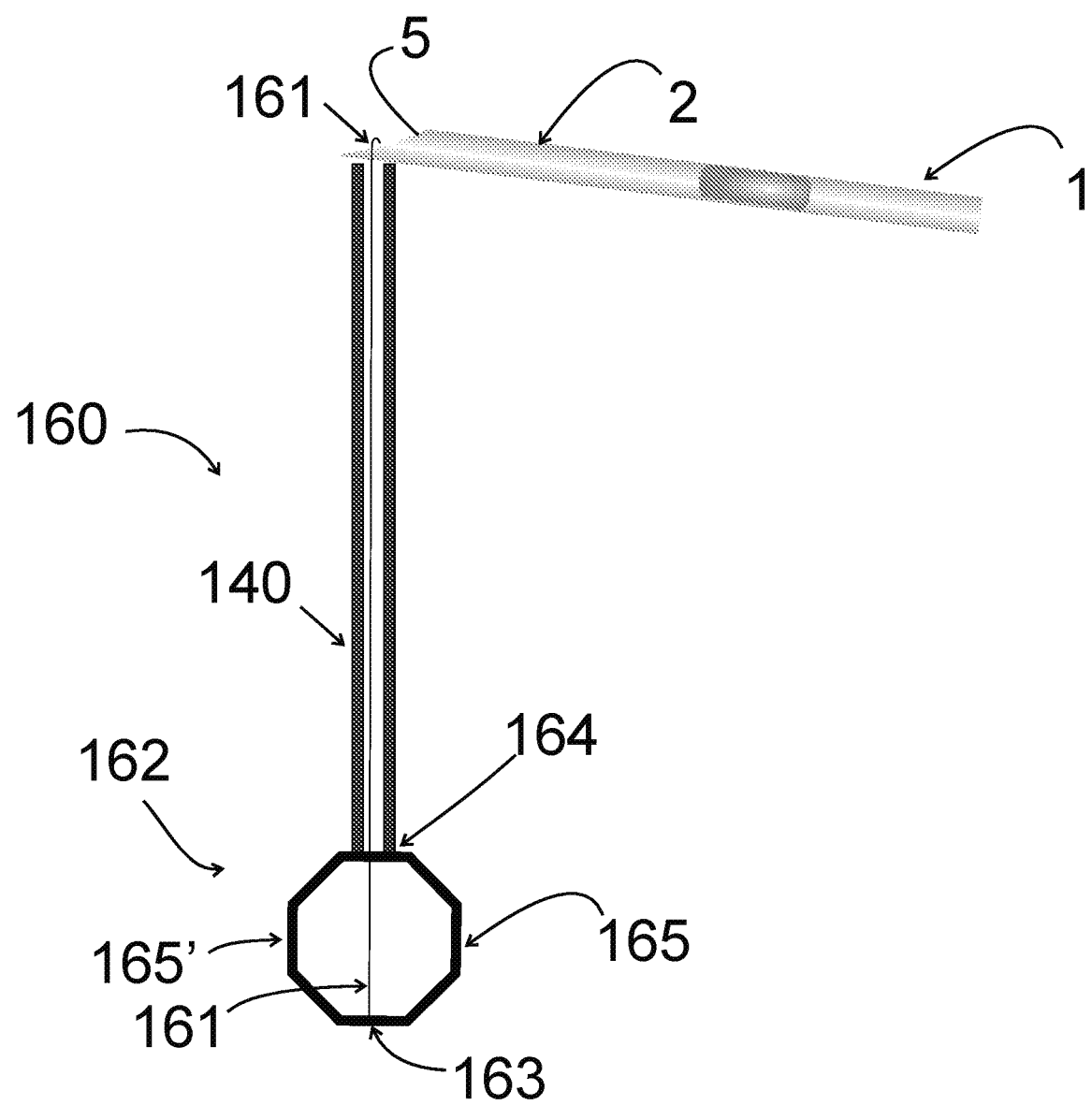
FIG. 16 shows another embodiment of an inserter tool.

FIG. 16 shows another embodiment of an inserter tool 160 having a thin filament 161 that extends down the channel of an inserter tube 140 (hypodermic tubing). The inserter tube 140 can be formed with the same or similar dimensions and mechanical properties as described above for the inserter rod 40. The inserter tool 160 also has an actuation mechanism similar to the embodiment of FIG. 15. In this embodiment, the filament 161 extends down the channel of the inserter tube 140 and is fastened to the lower end of a filament-form octagon 162 at point 163. The inserter tube 140 is attached to the filament-form octagon 162 at point 164. The filament-form octagon 162 can be made from a spring metal or spring polymer such as Delrin or Nylon. By pinching or otherwise compressing the filament-form octagon 162 at sides 165 and 165', the filament-form octagon 162 elongates axially causing the distal end of the filament 161 to pull (toward the proximal end of the inserter tube 140) through the tube 2 at or near the distal end 5 of the tube 2 in order to release or detach the tube 2 from the filament 161 and the inserter tube 140 and allow removal of the inserter tool 160 (including the filament 161 and the inserter tube 140) from the needle tract 24 while leaving the glaucoma shunt 1 in place. This octagonal shape is preferred as the filament 161 can be set with some tension on it to capture the tube 2. It can then be pinched or otherwise compressed to pull the filament 161 into the inserter tube 140 to release or detach the tube 2 from the filament 161 and the inserter tube 140. This embodiment can also be used with filament configurations shown in FIGS. 9-11.

As noted above, a needle 21 can been used to form tissue tract 24. Such needles can be a syringe needle (a hollow tubular) or a solid needle. However, in accordance with this description, a multi-bladed knife can also be used to form the tissue tract 24. More specifically, a multi-bladed knife can be used to provide a passageway through ocular tissue into which the glaucoma shunt 1 can be inserted for implantation thereof using the inserters and methods described above. By using the multi-bladed knife, rather than the needle 21, the tract 24 can be a combination of a tissue pocket as well as a tissue passageway that leads from the tissue pocket to the anterior chamber 23 of the eye. The glaucoma shunt 1 can be inserted through the tissue passageway such that the distal end 5 is positioned inside the anterior chamber 23 of the eye. The proximal end 6 of the tube 2 can be positioned in the tissue pocket to allow for drainage of aqueous humor through the lumen of the tube 2 and into tissue that surrounds the tissues pocket.

As will be described in greater detail below, the tissue pocket and the tissue passageway can be formed using a tissue tract-forming tool as shown in FIGS. 17A to 19B. As will be described in greater detail below, the tissue tract-forming tool includes a first blade portion having a double edge that forms the tissue passageway and a wider second blade portion having a double edge that forms the tissue pocket.

Figure 17A:
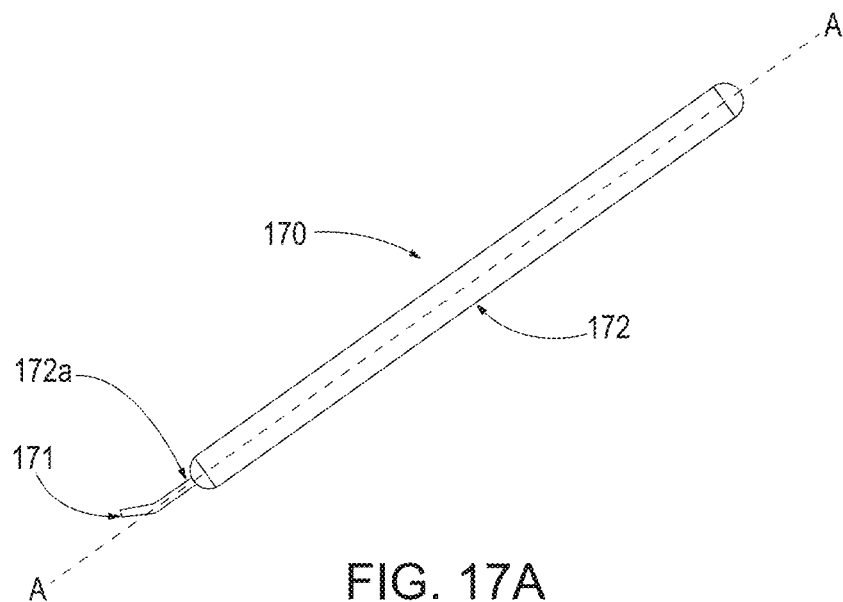
FIG. 17A is a side view of a tissue tract-forming tool in accordance with this disclosure.
Figure 17B:
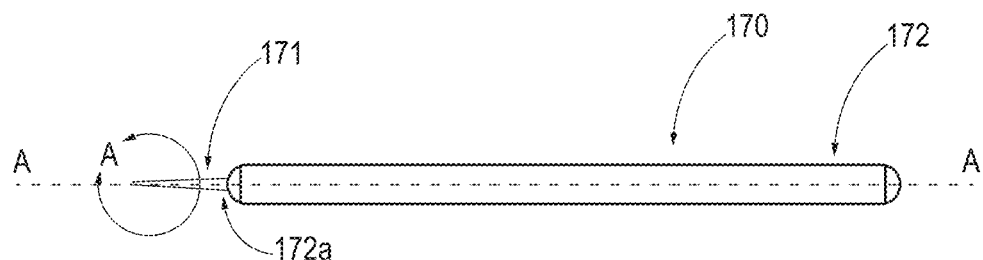
FIG. 17B is a plan view of the tool of FIG. 17A.
Figure 17C:
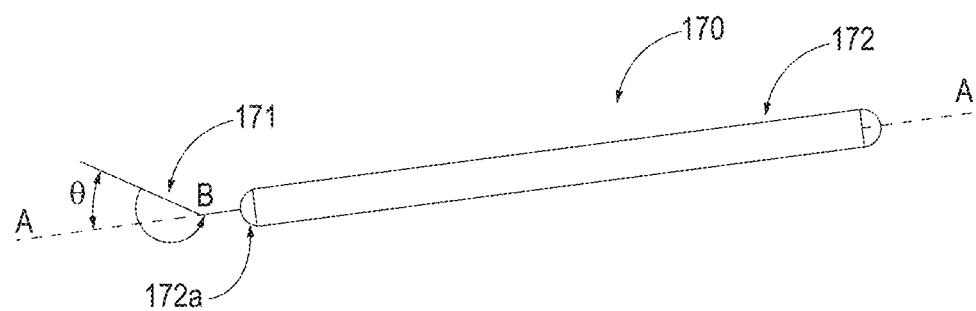
FIG. 17C is another side view of the tool of FIG. 17A.

FIGS. 17A to 17C show a tissue tract-forming tool 170 according to a first embodiment, which has an elongated handle 172 coupled to the two-stepped knife 171, which extends from a distal end 172a of the handle 172. The knife 171 and the handle 172 extend longitudinally along an axis A-A in FIG. 17B. The knife 171 can be made from any material knives are typically made from, for example, stainless steels, chromium-cobalt-nickel, titanium, etc.

As shown in FIG. 17C, the knife 171 may be pre-bent so that a distal portion of the knife 171 is bent at a non-zero angle (preferably an acute angle) with respect to the axis A-A. In the embodiment shown in FIG. 17C, the angle is about 30 degrees.

Figure 17D:
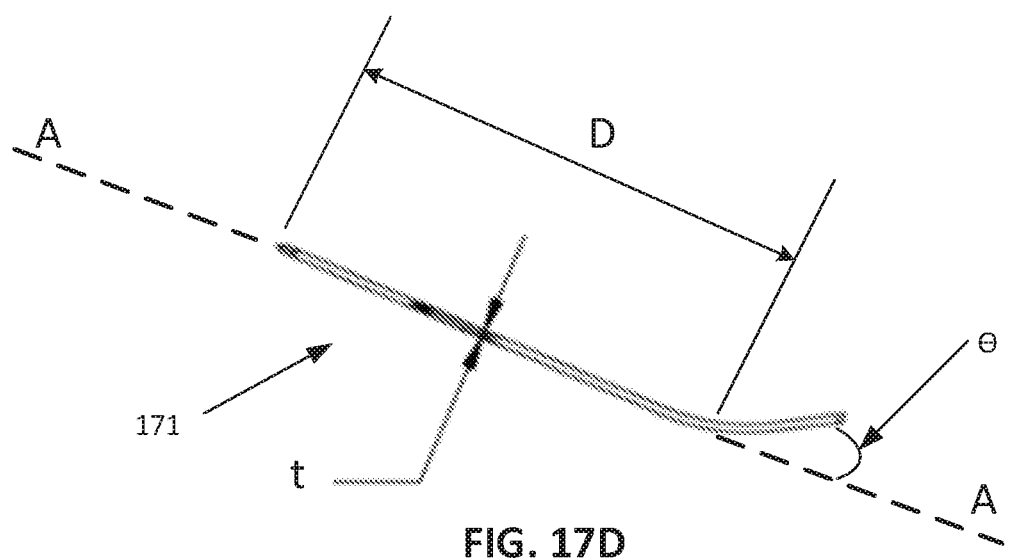
FIG. 17D is an exploded view of a portion of the tool of FIG. 17C.

With reference to FIG. 17D, the knife 171 has a thickness. "t", which can be between 0.003 inch to 0.010 inch, but may preferably be about 0.005 inch. Also, the distance "D" along the knife 171 from its tip to the location of the bend is about 0.25 inch.

Figure 17E:
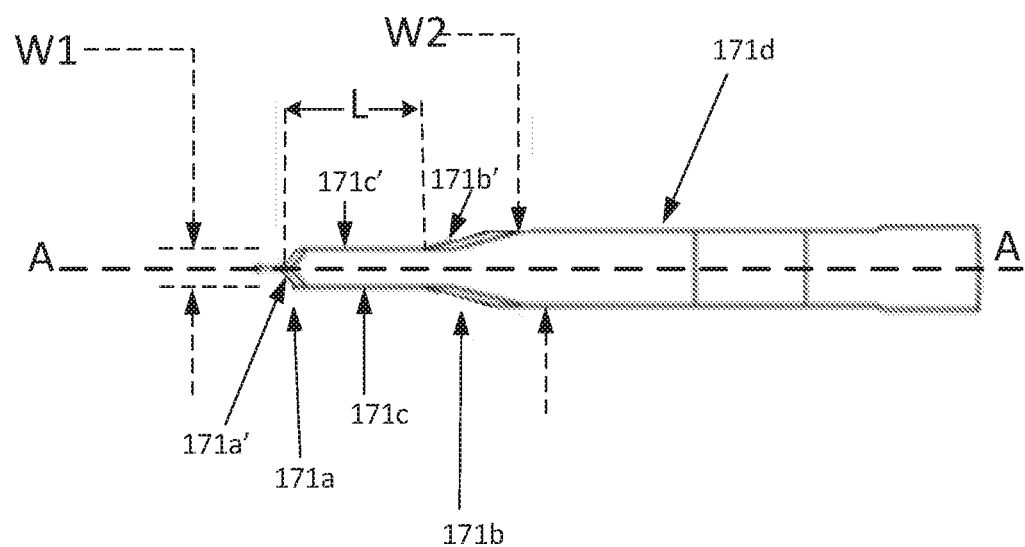
FIG. 17E is an exploded view of a portion of the tool of FIG. 17B.

As shown in greater detail in FIG. 17E, the knife 171 includes the first knife portion 171a and the second knife portion 171b spaced axially from the first knife portion 171a by an intermediate portion 171c. The first and second knife portions 171a and 171b have staggered maximal widths (measured in a direction transverse to the axis A-A) W1 and W2, respectively. The first width W1 may be 0.015 to 0.025 inch, and preferably is about 0.020 inch. The second width W2 may be 0.03 to 0.05 inch, and preferably is about 0.04 inch. The intermediate portion 171c extends a length L along the axis A-A, which can be determined based on the length of the tissue passageway that will be formed by the leading edge 171a ahead of the tissue pocket formed by the trailing edge 171b. In one or more embodiments, the length L is about 2.2+/−0.2 mm. Other suitable lengths can be used if desired.

In one embodiment, the first width W1 is related to the dimension(s) (e.g., diameter) of tube 2. For example, the diameter of the tube 2 may be 0.013 inch, so that the circumference of the tube 2 is 0.04 inch (0.013×pi). The first width W1 may be 0.050 inch 0.020+2×0.005). The diameter of the tube 2 may be 20% smaller than the first width W1 to facilitate introduction of the tube 2 through ocular tissue. The second width W2 may also be related to the dimension(s) of fin 3 of the glaucoma drainage device 1. For example, the wingspan (e.g., maximum diameter) of the fin 3 may be 0.043 inch so that its circumference is 0.113 inch (2×0.043+2×0.013). The circumference of blade 171b at its widest point may be 0.090 inch (2×0.04+2×0.005) so that the knife 171b circumference is therefore 20% smaller than the circumference of the fin 3. This allows the fin 3 to wedge securely into the pocket famed in the sclera by blade 171b to prevent migration of the tube 2 and periannular leakage.

The first knife portion 171a has a first set of opposed knife edges 17 that each extend from a leading end to a trailing end, which is the widest part of the first knife portion 171a. The knife edges 171a' are configured to cut ocular tissue and form the tissue passageway described above when the knife 171 is inserted into an eye. The first knife edges 171a' extends at a first angle with respect to the axis A-A, as shown in FIG. 17E. At the distal end of the first knife edge 171a', there is a transition to a straight edge 171c' of the intermediate portion 171c which extends parallel to the axis A-A between the first knife portion 171*a* and the second knife portion 171*b*. The straight edge 171*c*' may be a dull surface that is not suitable to cut ocular tissue, but may be configured to cut tissue in at least one embodiment. The straight edge 171*c*' transitions to a leading end of a second knife edge 171*b*' of the second knife portion 171*b*. The second knife edge 171*b*' extends at a second angle with respect to axis A-A to a trailing end at the widest part of the second knife edge 171*b*'. The second knife portion 171*b* is wider than the first knife portion 171*a* (measured perpendicular or radially with respect to axis A-A in FIG. 17E) so that the second knife edge 171*b*' is stepped or staggered in relation to the first knife portion 171*a*. The second knife edge 171*b*' is sharp and configured to cut ocular tissue to form the abovementioned tissue pocket. In FIG. 17E, the knife 171 has a straight edge 171*d* that extends proximally from the trailing end of the second knife edge 171*b*' and extends parallel to axis A-A.

Figure 18:
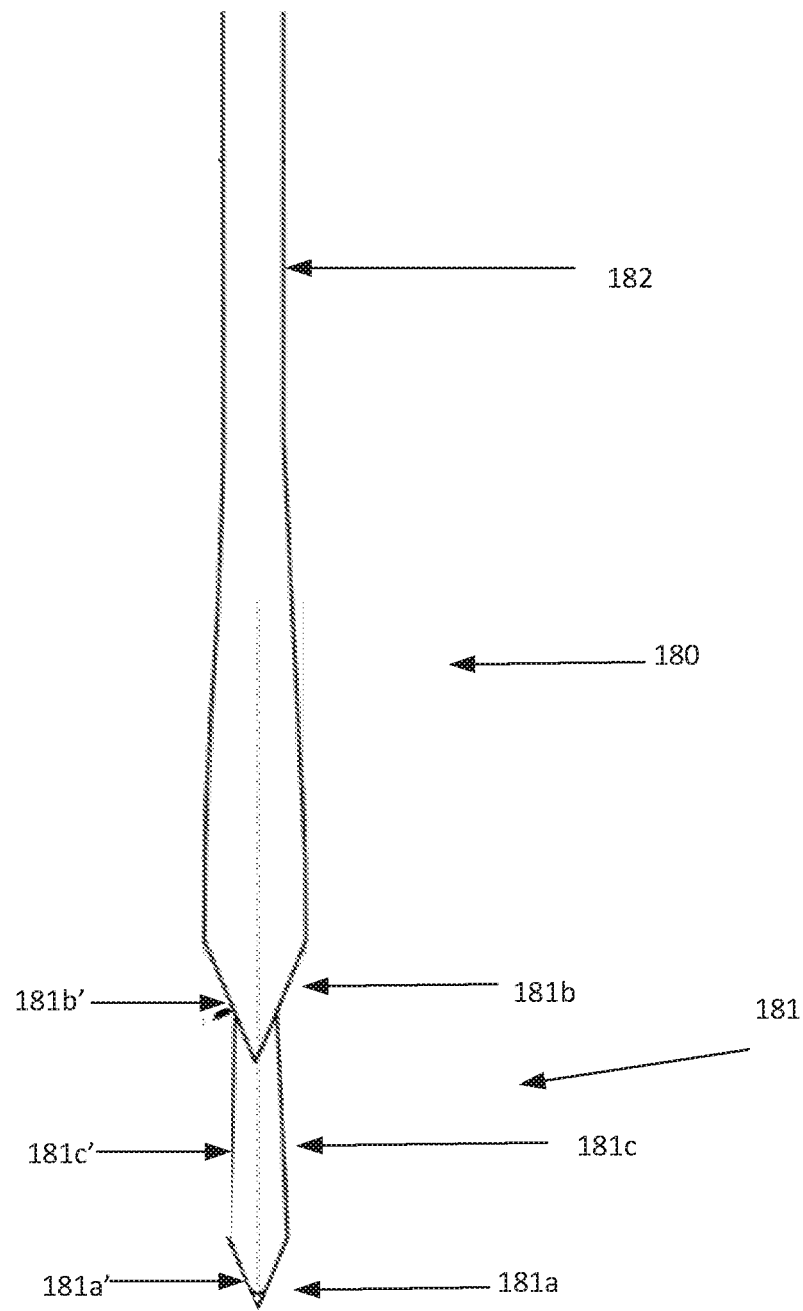
FIG. 18 is a plan view of another tissue tract-forming tool in accordance with this disclosure.

FIG. 18 shows another embodiment of a tool 180 for use in forming a tissue tract and pocket in the eye. Similar features to tool 170 are denoted by the same reference numbers, but incremented by "10". One difference between tool 170 and tool 180 is that the straight edge 181*c*' of the intermediate portion 181*c* between the first knife portion 181*a* and the second knife portion 181*b* is not parallel with the axis A-A, but instead is tapered from the first knife portion 181*a* to the second knife portion 181*b*. Also, the knife 181 has a straight, tapered edge that extends distally from a trailing end of the second knife edge 181*b*' to the handle 182. The tapering of the knife 181 proximally of each of the first and second knife portions facilitates manufacturing (if forged, it is easier to pull out of a mold with a taper) and minimizes drag while cutting ocular tissue.

Figure 19A:
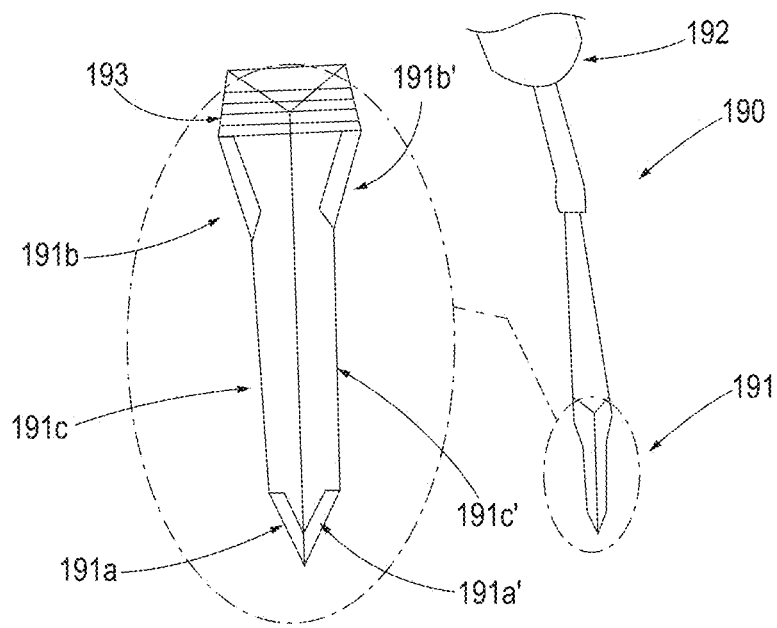
FIG. 19A is a plan view of another tissue tract-forming tool in accordance with this disclosure and an exploded view of a knife of the tool.

FIG. 19A shows another embodiment of a tool 190 for use in forming a tissue tract and pocket in eye. Similar features to tool 170 are denoted by the same reference numbers, but incremented by "20". One difference between the tool 170 and tool 190 is that the straight edge 191*c*' of the intermediate portion 191*c* between the first knife portion 191*a* and the second knife portion 191*b* is not parallel with the axis A-A, but instead is tapered from the second knife portion 191*h* to the first knife portion 191*a*, which is the reverse arrangement of the knife 181 of tool 180. This arrangement of the knife 191 facilitates manufacturing (if forged, it is easier to pull out of a mold with a taper) and minimizes drag while cutting ocular tissue.

Also, FIG. 19A shows indicia 193, in the form of graduated lines, on the surface of the knife across the widest portion of knife edges 191*b*' and at 0.5 mm increments proximal to this point. The graduated lines may be used as depth guides for the user to denote how far to insert the knife 191 into the ocular tissue.

Figure 19B:
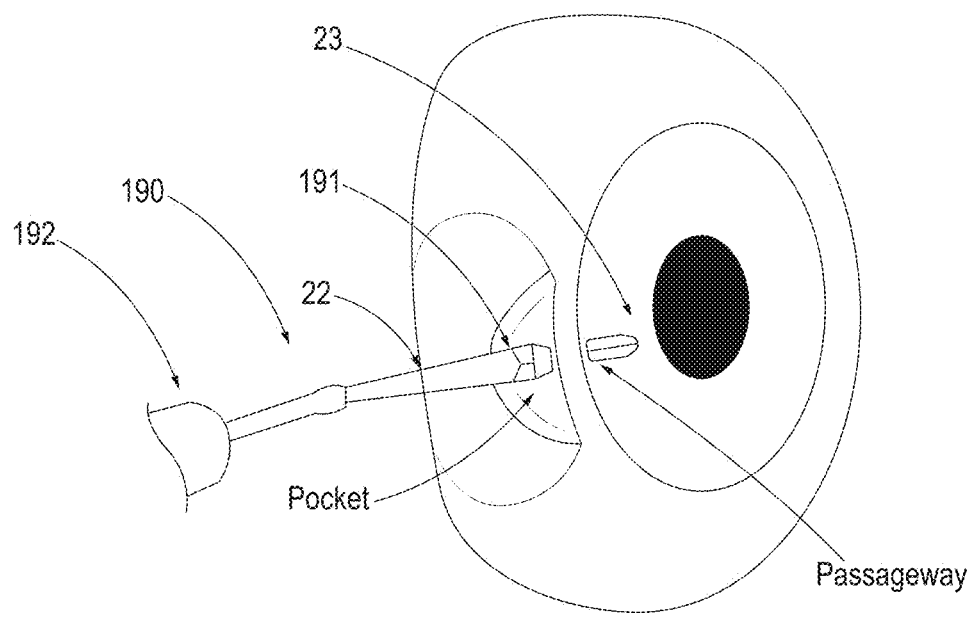
FIG. 19B shows the tool of FIG. 19A inserted into a tissue tract formed in an eye.

FIG. 19B shows how the tool 190 may be used to form the tissue passageway and pocket. A user holding the handle 192 introduces the first knife portion 191*a* into the eye and advances the first knife portion 191*a* under the limbus 22 until the first knife portion 191*a* is in the anterior chamber 23. The second knife portion 191*b*, spaced proximally behind the first knife portion 191*a*, cuts a wider path behind the first knife portion 191*a* and forms a pocket behind the first knife portion spaced by the predetermined insertion distance. When the tissue passageway and pocket are formed, the tool 190 can be removed from the eye, leaving behind the tissue passageway that leads from the tissue pocket to the anterior chamber 23. The glaucoma shunt 1 may then be implanted into the tissue passageway as described above.

There have been described and illustrated herein several embodiments of an ocular implant inserter and a method of use. While particular embodiments of the inserter and method have been described, it is not intended that the invention be limited thereto, as it is intended that the invention be as broad in scope as the art will allow and that the specification be read likewise. Thus, while particular arrangements of the inserter have been disclosed, it will be appreciated that other arrangements may be used as well. In addition, while particular types of materials for the elongate member of the inserter and knife have been disclosed, it will be understood that other suitable materials can be used. Moreover, while particular configurations have been disclosed in reference to a handle and actuator mechanism for releasing or detaching the inserter from the tube of the glaucoma drainage device in its implanted configuration, it will be appreciated that other configurations could be used as well. Furthermore, while particular configurations have been disclosed in reference to a filament holding the drainage device in place, the distal end of the filament can be flattened or beaded to prevent the drainage device from falling off the inserter during shipping and handling, it will be appreciated that other configurations could be used as well. It will therefore be appreciated by those skilled in the art that yet other modifications could be made to the provided invention without deviating from its spirit and scope as claimed.

What is claimed is:

1. A glaucoma treatment system comprising:
   a glaucoma drainage device including an elongated tube extending from a distal end to a proximal end, the elongated tube having a tubular wall with an outer surface and an inner surface defining an elongated lumen extending from the distal end to the proximal end; and
   an inserter including an elongate member with a filament extending from beyond the distal end of the elongate member, wherein the filament is configured to detachably couple a distal portion of the glaucoma drainage device to the elongate member of the inserter;
   wherein the filament is secured at or near the distal end of the elongate member and configured to pierce at least the outer surface of the tubular wall of the tube of the glaucoma drainage device at or near the distal end of the tube of the glaucoma drainage device with the filament extending along a path through the tubular wall that is different from the lumen of the tube for detachably coupling the distal portion of the glaucoma drainage device to the elongate member of the inserter.

2. The system according to claim 1, wherein:
   in a coupled configuration wherein the distal portion of the glaucoma drainage device is detachably coupled to the elongate member of the inserter, the filament extends along the path through the tubular wall of the tube of the glaucoma drainage device at or near the distal end of the tube of the glaucoma drainage device.

3. The system according to claim 1, wherein:
   the elongate member of the inserter is rigid, and the tube of the glaucoma drainage device is flexible.

4. The system according to claim 1, wherein:
   a distal portion of the filament is bent toward the proximal or distal end of the tube of the glaucoma drainage device; or
   the distal portion of the filament is bent in a pig-tail or loop that secures the tube of the glaucoma drainage device to the elongate member of the inserter; or the distal portion of the filament is beaded or flattened to secure the tube of the glaucoma drainage device to the elongate member of the inserter.

5. The system according to claim 1, wherein:
the filament and the elongate member of the inserter are configured for relative movement to release or detach the tube of the glaucoma drainage device from the filament and the elongate member of the inserter.

6. The system according to claim 5, wherein:
the elongate member comprises an inserter tube that defines an internal channel extending axially, the filament extending axially in the channel of the inserter tube, the filament and the inserter tube configured for relative axial movement, wherein the filament is configured to move toward the proximal end of the inserter tube to release or detach the tube of the glaucoma drainage device from the filament and the inserter tube of the inserter.

7. The system according to claim 6, further comprising:
a hub positioned adjacent the proximal end of the inserter tube, wherein a proximal end of the filament is secured to the hub;
a retainer secured to the outer surface of the inserter tube at an intermediate position between the distal end of the inserter tube and the hub; and
a spring surrounding the outer surface of the inserter tube between the hub and the retainer, the hub and spring being configured for displacement relative to the inserter tube, and wherein the spring is biased in compression to produce tension in the filament to cause the filament to secure the distal portion of the tube of the glaucoma drainage device to the distal end of the inserter tube in a first configuration of the hub and the spring.

8. The system according to claim 7, wherein:
the hub and spring are reconfigurable from the first configuration to a second configuration by moving the hub and spring towards the retainer thereby causing the filament to move axially in the channel of the inserter tube toward the proximal end of the inserter tube to release or detach the tube of the glaucoma drainage device from the filament and the inserter tube of the inserter.

9. The system according to claim 6, further comprising:
a scissor mechanism coupled between a proximal end of the inserter tube and to a proximal end of the filament, the scissor mechanism having handles operable to move the filament axially in the channel of the inserter tube toward the proximal end of the inserter tube to release or detach the tube of the glaucoma drainage device from the filament and the inserter tube of the inserter.

10. The system according to claim 6, further comprising:
a filament-form actuator connected between a proximal end of the inserter tube and to a proximal end of the filament, the actuator configured to be compressed to move the filament axially in the channel of the inserter tube toward the proximal end of the inserter tube to release or detach the tube of the glaucoma drainage device from the filament and the inserter tube of the inserter.

11. The system according to claim 1, wherein:
the glaucoma drainage device has external fixation means extending radially outward from the tube of the glaucoma drainage device and located between the distal and proximal ends of the tube of the glaucoma drainage device.

12. The system according to claim 11, wherein:
the fixation means is comprised of a protrusion that extends along a portion of the length of the tube of the glaucoma drainage device.

13. The system according to claim 1, wherein:
a distal part of the tube of the glaucoma drainage device is secured or tethered to the elongate member of the inserter.

14. The system according to claim 13, wherein:
a tether filament or a sheath secures or tethers the proximal part of the tube of the glaucoma drainage device to the elongate member of the inserter.

15. The system according to claim 1, wherein:
the elongate member of the inserter comprises a solid rod or tube.

16. The system according to claim 1, wherein:
the elongate member of the inserter has an outer diameter between 0.006 inch and 0.020 inch.

17. The system according to claim 16, wherein:
the elongate member of the inserter is a tube having an inner diameter between 0.002 inch and 0.012 inch.

18. The system according to claim 1, wherein:
the elongate member of the inserter is configured to withstand a concentric compressible axial load between 0.004 pound force to 0.5 pound force without experiencing inelastic deformation.

19. A method for treating glaucoma with an implantable glaucoma drainage device, the method comprising:
providing a glaucoma drainage device including a tube extending from the distal end to the proximal end, the tube having a tubular wall with an outer surface and an inner surface defining an elongated lumen extending from the distal end to the proximal end;
providing an inserter including an elongate member with a filament extending from beyond the distal end of the elongate member, wherein the filament detachably couples a distal portion of the tube of the glaucoma drainage device to the elongate member of the inserter, wherein the filament is secured at or near the distal end of the elongate member and pierces at least the outer surface of the tubular wall of the tube of the glaucoma drainage device at or near the distal end of the tube of the glaucoma drainage device with the filament extending along a path through the tubular wall that is different from the lumen of the tube for detachably coupling the distal portion of the glaucoma drainage device to the elongate member of the inserter;
forming a tissue passageway in the eye leading to the anterior chamber of the eye;
introducing the inserter and the distal portion of the tube of the glaucoma drainage device together through the tissue tract by pushing the inserter into and through the tissue tract;
positioning the tube of the glaucoma drainage device at a desired implanted position within the tissue tract; and
with the tube of the glaucoma drainage device positioned at the desired implanted position, decoupling the filament of the inserter from the distal portion of the tube of the glaucoma drainage device.

20. The method according to claim 19, wherein:
decoupling the filament includes retracting the elongate member of the inserter out of the tissue tract while holding the glaucoma drainage device in place at the desired position.

21. The method according to claim 19, wherein:
decoupling the filament includes moving the filament relative to the elongate member of the inserter proximally toward the proximal end of the elongate member.

22. The method according to claim 19, further comprising:
removing the inserter from the tissue passageway after decoupling the filament.

23. The system according to claim 1, further comprising:
a knife for forming a tissue tract through which an inserter and glaucoma drainage device are inserted, the knife having a plurality of blades, the knife extending from a distal end to a proximal end along a knife axis, the knife having a first portion, a second portion, and an intermediate portion extending between the first and second portions, wherein
the first portion is located at the distal end and the second portion being spaced proximally from the first portion by the intermediate portion, the intermediate portion having a dull edge that is not configured to cut ocular tissue,
the first portion having a first set of blades that extend at a first angle relative to the knife axis from a first leading blade end to a first trailing blade end at a first transverse distance from the knife axis, and
the second portion having a second set of blades that extend at a second angle relative to the knife axis from a second leading blade end to a second trailing blade end at a second transverse distance from the knife axis that is larger than the first transverse distance.

24. The system according to claim 23, wherein:
the first transverse distance is between 0.015 to 0.025 inch and the second transverse distance is between 0.03 to 0.05 inch.

25. The system according to claim 24, wherein:
the first and second angles are non-zero, acute angles.

26. The system according to claim 24, wherein:
the intermediate portion has a length along the knife axis that is 2.0 mm to 2.4 mm.

27. A glaucoma treatment system comprising:
a glaucoma drainage device including an elongated tube extending from a distal end to a proximal end, the elongated tube having a tubular wall with an outer surface and an inner surface defining an elongated lumen extending from the distal end to the proximal end; and
an inserter including an elongate member with a filament extending from beyond the distal end of the elongate member, wherein the filament is configured to detachably couple a distal portion of the glaucoma drainage device to the elongate member of the inserter;
wherein the filament is secured at or near the distal end of the elongate member and pierces at least the outer surface of the tubular wall of the tube of the glaucoma drainage device at or near the distal end of the tube of the glaucoma drainage device with the filament extending along a path through the tubular wall that is different from the lumen of the tube; and
wherein the glaucoma drainage device includes one or more protrusions or fins spaced from the distal and proximal ends of the tube and extending radially outward beyond the outer surface of the tube.

28. The system according to claim 27, wherein:
the tubular wall defines an angled distal end that is oriented at a non-perpendicular angle relative to the central axis of the lumen of the tube, and the path of the filament extends through the angled distal end.

29. The method according to claim 19, wherein:
the tubular wall defines an angled distal end that is oriented at a non-perpendicular angle relative to the central axis of the lumen of the tube, and the path of the filament extends through the angled distal end.

30. The method according to claim 19, wherein:
with the filament detachably coupling the distal portion of the glaucoma drainage device to the inserter, the pushing of the inserter into and through the tissue tract pulls the tube for advancing the tube distally through the tissue tract.

31. The system according to claim 1, wherein:
the tubular wall defines an angled distal end that is oriented at a non-perpendicular angle relative to the central axis of the lumen of the tube, and the path of the filament extends through the angled distal end.

* * * * *